United States Patent [19]
Janz et al.

[11] Patent Number: 5,321,014

[45] Date of Patent: Jun. 14, 1994

[54] MOLECULAR ENCAPSULATION AND DELIVERY OF ALKENES ALKYNES AND LONG CHAIN ALKANES, TO LIVING MAMMALIAN CELLS

[75] Inventors: Siegfried Janz, Bethesda; Emily Shacter, Kensington, both of Md.

[73] Assignee: The United States of America as represented by the Department of Health and Human Services, Washington, D.C.

[21] Appl. No.: 723,240

[22] Filed: Jun. 28, 1991

[51] Int. Cl.$^5$ ............... C12Q 1/02; A61K 31/715
[52] U.S. Cl. ............................ 514/58; 536/103; 435/29
[58] Field of Search ............... 514/58; 536/103; 435/29

[56]  References Cited

U.S. PATENT DOCUMENTS

| | | | |
|---|---|---|---|
| 2,827,452 | 3/1958 | Schlenk et al. | 514/58 |
| 2,959,580 | 11/1960 | Schlenk et al. | 536/103 |
| 3,061,444 | 10/1962 | Rogers et al. | 536/103 |
| 3,465,055 | 9/1969 | Gleim et al. | 536/103 |
| 3,846,551 | 11/1974 | Mifune et al. | 514/58 |
| 4,024,223 | 5/1977 | Noda et al. | 514/770 |
| 4,228,160 | 10/1980 | Szejtli et al. | 514/58 |
| 4,228,160 | 10/1980 | Szejili et al. | 536/103 |
| 4,834,985 | 5/1989 | Elger et al. | 424/488 |
| 4,956,351 | 9/1990 | Mesens et al. | 514/58 |
| 5,007,966 | 4/1991 | Hedges et al. | 514/58 |
| 5,019,563 | 5/1991 | Hunter et al. | 536/103 |
| 5,070,081 | 12/1991 | Majid et al. | 514/58 |
| 5,079,000 | 1/1992 | Takahashi et al. | 514/58 |

FOREIGN PATENT DOCUMENTS

| | | |
|---|---|---|
| 53-101531 | 9/1978 | Japan . |
| 58-21602 | 2/1982 | Japan . |
| 62-120344 | 6/1987 | Japan . |
| 1-287094 | 11/1989 | Japan . |
| 2090738 | 7/1982 | United Kingdom . |

Primary Examiner—Ronald W. Griffin
Attorney, Agent, or Firm—Susan S. Rucker

[57] ABSTRACT

A complex of a cyclodextrin and an alkane, alkene, alkyne, aromatic compound, etc. can be prepared according to the method of the present invention. These complexes can be delivered to prokaryotic and eukaryotic cells, tissues, and organs in vitro and in vivo. In this manner, the toxic, genotoxic, and mitogenic effects of these compounds can be determined. Ternary complexes further including one or more biologically active molecules in addition to an alkane, etc. can be employed to determine the modulatory effects of such biologically active molecules on these alkanes, etc.

27 Claims, 11 Drawing Sheets

MOLECULAR ENCAPSULATION AND DELIVERY OF ALKENES ALKYNES AND LONG CHAIN ALKANES, TO LIVING MAMMALIAN CELLS

BACKGROUND OF THE INVENTION

1. Field of the Invention

The present invention relates to the interaction between hydrophobic compounds and mammalian cells. It includes the areas of in vitro testing of the effects of hydrophobic compounds on cells for biomedical research purposes, including cancer research and genotoxicity assessment, and for the production and application of new pharmaceutical compositions containing hydrophobic substances for administration in liquid or powder form.

2. Description of Related Art

The study of aliphatic hydrocarbons (alkanes) has become increasingly important in biomedical research (1-3). The alkane components of mineral paraffin oils are implicated in a number of human pathologic conditions such as mineral oil pneumonia, folliculitis of the skin, oleogranuloma (paraffinoma), and systemic focal lipidosis (4). Human exposure to mineral paraffin oils comes from workplace contaminants (5), environmental pollutants (6), food (7), and medications (8). Particular interest in the biological actions of alkanes derives from the fact that in genetically susceptible inbred strains of mice (BALB/c and NZB), intraperitoneal injection of mineral oils such as the isoalkane pristane (2,6,10,14-tetramethylpentadecane) induces a malignant B cell lymphoma (plasmacytoma, 9). Over the years, pristane-induced plasmacytomagenesis has become the most intensively studied prototype for plasma cell tumorigenesis (reviewed in 10 and 11).

Pristane and other lipophilic alkanes are practically immiscible with aqueous media (12) required for cell growth and viability. However, when pristane is injected and then withdrawn from the peritoneal cavity of a mouse it appears as an emulsion even after only a few days. Emulsification of pristane in vivo is probably facilitated by amphiphilic molecules (e.g., fatty acids, fatty alcohols, phospholipids, and proteins) that are present in abundance in the inflammatory environment that results from injection of the oil. In a conventional plasmacytoma induction protocol, 1.5 ml of pure pristane ($\approx$4.4 mmol) are injected. The oil is gradually incorporated into a fixed inflammatory tissue (oil granuloma) but can still be found in large quantities in the peritoneal fluid for months following its injection. Given that some sort of emulsification and hence solubilization of pristane takes place in vivo, it is clear that cells are exposed to pristane over a prolonged period of time. Although pristane is thought to act indirectly by inducing chronic inflammatory conditions which somehow permit plasmacytomagenesis (11), direct biological effects of the alkane on cells may also contribute to the tumorigenic process. Some direct biological effects of pristane have been described (7).

Pristane (2,6,10,14-tetramethylpentadecane) causes numerous detrimental effects in animals (22, 23, 24, 25). It promotes skin carcinogenesis in C3H mice (26) and the development of 3-methylcholanthrene induced lymphoid malignancies in Copenhagen rats (27). Furthermore, pristane induces histiocytomas in BALB/c and BALB/Mo mice (28) and plasmacytomas in BALB/cAnPt mice (29). Murine plasmacytomagenesis is by far the most widely studied tumor system involving pristane (reviewed in 10, 11). Hence, much of the current interest in this simple compound, an isoprenoid $C_{19}$-isoalkane, is derived from the desire to better understand plasmacytomagenesis in mice.

The tumor inducing activity of pristane, thought to be a non-genotoxic, "complete" carcinogen, is still poorly understood. This is reflected by several diverse hypotheses on its putative effects in vivo. Changes in the conformation of DNA in lymphocytes (30) and hybridoma cells (31) after incorporation of pristane have been observed fluorometrically with propidium iodide. A subsequent fluorescence polarization study revealed pristane-induced changes in the membrane fluidity of rat lymphocytes (32). The generation of oxidation products of pristane by reactive oxygen intermediates (33) had been proposed as a possible additional component of the action of pristane under the conditions of a prolonged inflammation in vivo (34). Immunosuppression (35, 36, 37) and formation of a specific histologic matrix for tumor origin and development (38) after the intraperitoneal administration of pristane may contribute to tumorigenesis through different pathways. Whether or not pristane metabolites that may be generated in vivo (39) are involved in the tumor inducing activity of pristane is presently completely unclear.

In early experiments, attempts were made to solubilize and deliver pristane to cells by using conventional solubilization methods such as mixing with organic solvents and surfactants or by using liposomes of different compositions (13). Both methods were found to be unacceptable. The key constraint derived from the need to deliver sufficient amounts of pristane without exposing the mammalian tester cells to toxic or "bioactive" solvents.

There is no evidence that the complexation of pristane, or any other alkane, with cyclodextrins has ever been used for delivering these compounds in biological assay systems. The predominant examples of the employment of cyclodextrins as solubilizers in biomedicine are in pharmaceutical applications of drug complexation and delivery by cyclodextrins, including non-steroidal anti-inflammatory drugs, steroids, fat-soluble vitamins, prostaglandins, barbiturates, cardiac glycosides, etc. (reviewed in 18). In addition, there are numerous applications of cyclodextrins in the chemical industry such as for separation and resolution of enantiomers as well as for chromatographic separations on cyclodextrin polymers (reviewed in 15 and 16).

Conventional methods of solubilizing alkanes in watery media rely either on the use of organic solvents with or without surfactants, or on use of vesicles such as unilamellar or multilamellar liposomes. The employment of organic solvents imposes severe biological drawbacks because many of them are highly toxic and may produce artifacts even at very low concentrations. Moreover, organic solvents do not guarantee that lipophilic compounds will remain dissolved after further dilution into aqueous media. Although the solubilizing properties of organic solvents may potentially be improved by combining them with surface active compounds (biological detergents, tensids and co-tensids), surfactants frequently alter and eventually disrupt cell membranes. Moreover, it has been shown that the extent of the adsorption of surfactants at oil-water interfaces is largely determined by the nature of the hydrocarbon oil itself (e.g., 87), indicating that the solubilization system must be optimized for each individual alkane under consideration. This would necessitate rather extensive solubilization studies prior to any biological testing. Despite the drawbacks of employing organic solvents and surfactants to introduce alkanes into aqueous media, they are still widely used.

The preparation of lipid vesicles is another widely and successfully used method to deliver highly lipophilic compounds to mammalian cells. Nonetheless, this approach also requires careful consideration of potential artifacts. Problems associated with using liposomes are dependent on the composition of the vesicles. For example, lipid exchange or fusion between vesicles and target cells can alter many properties of the target cell membrane, such as its fluidity or the mobility and activity of membrane bound proteins involved in signal transduction pathways Hence, specific effects of the alkane of interest may be obscured by effects of the liposome itself, thus complicating interpretation of the results. A number of practical disadvantages in employing lipsome vesicles may also be encountered such as problems of reproducibility between different liposome preparations or stability and storage problems. Pristane can be dissolved in unilamellar liposomes, but the effectiveness of the liposomes is dependent upon the phospholipids employed for their preparation. Hence, the solubilization vehicle itself is a variable in the experiments. Thus there is a need to find an inert vehicle to deliver pristane and other alkanes and hydrophobic substances to cells.

SUMMARY OF THE INVENTION

The induction of plasmacytomas by pristane has provided a useful model system in cancer research, genetics, and immunology, and has led to important biotechnological applications such as hybridoma technology and monoclonal antibody production.

In spite of considerable progress in our understanding of the pathogenesis of murine plasmacytomas, the precise role of the plasmacytomagenic agent pristane is poorly defined, partly because of a continuous failure to find effective methods to test the effects of this hydrophobic compound on mammalian cells in vitro. Pristane and other lipophilic alkanes are immiscible with the aqueous environment required for mammalian cells to function properly. Initially, attempts to overcome this problem employed either conventional solubilization methods such as mixing with organic solvents and surfactants, or the use of liposomes of different compositions. All attempts to design a compromise between delivering sufficient amounts of pristane on the one hand and meeting the requirements of sensitive mammalian tester cells on the other hand contained unacceptable methodological limitations.

One goal of the present work is to elucidate the plasmacytomagenic activity of pristane at the cellular level. It is likely that at least part of the effects caused by pristane are connected with alterations of membrane properties. Yet, quantitative data on the uptake of pristane by lipid membranes are not available. As described below, the incorporation of pristane into model membranes was studied via three physico-chemical methods. Experiments were aimed at quantifying the uptake of pristane into model membranes and determining the influence of the mode of solubilization of pristane on its incorporation into lipid bilayers. For the latter, two methods were compared: a novel solubilization procedure for pristane in $\beta$-cyclodextrin ($\beta$-CyD), and the conventionally used method of dissolving pristane in the organic solvent dimethyl sulphoxide (DMSO). By employing NMR techniques, the present inventors also attempted to i) localize pristane within the membrane, ii) investigate changed membrane properties such as altered mobilities and conformations of lipid headgroups and fatty acids, and iii) study pristane induced lamellar-hexagonal phase transitions. The results described below should allow better comparison of the effects of pristane on lipid bilayers to the effects of other membrane-targeted compounds. This should facilitate development of new approaches to studying the interaction of pristane, other alkanes, alkenes, and alkynes with mammalian cells vitro.

In applying knowledge from the area of clathrate chemistry, which describes the interactions between so-called host and guest molecules (14), the present inventors devised a new, effective, and simple method of solubilizing pristane by forming a monomolecular inclusion complex with $\beta$-cyclodextrin. Cyclodextrins are ring-shaped oligomers of D-glucose which have a hydrophobic cavity and a hydrophilic surface. They are presently used in numerous processes in the chemical industry (reviewed in 15 and 16), and are increasingly employed for pharmaceutical applications such as drug complexation and delivery (17, 18). The molecular encapsulation of pristane into the hydrophobic cavity of a $\beta$-cyclodextrin molecule represents an innovative and superior concept for delivering this alkane to living mammalian cells in vitro. Moreover, this approach holds great promise for biological testing of a whole range of other straight and branched chained alkanes, alkenes, and alkynes that are also of interest in cancer research (19–21). Thus, the formation of cyclodextrin-/alkane inclusion complexes should enable the development of a number of new and important applications both for basic research on other alkanes (e.g., cancer research) and for applied research, such as in risk assessment for environmental and occupational health purposes (e.g., genotoxicity testing). Finally, this approach may ultimately lead to new product developments in biotechnology, e.g., the manufacturing of new alkane preparations with qualitatively different physiochemical properties compared to the parent compounds (e.g., alkanes in the form of ready-to-use water-soluble powders).

The preparation of $\beta$-cyclodextrin/pristane inclusion complexes may serve as a new and alternative system for testing the effects of pristane and other hydrophobic compounds on mammalian cells in vitro. The same approach should also be well suited for improving bioavailability of n-alkanes with chain lengths similar to that of pristane such as n-dodecane, n-tetradecane, and n-hexadecane. These compounds are of interest in cancer research because of their promoter effects in skin carcinoma model systems. The preparation of inclusion complexes with different natural, substituted, and polymerized cyclodextrins also holds future promise both for optimization of the delivery of pristane to living cells and for new applications for studying other alkanes, alkenes, and alkynes in the field of biomedical research.

Accordingly, it is an object of the present invention to provide a complex of a cyclodextrin and an alkane, an alkene, or an alkyne. Said complex may further contain a biologically active molecule other than said alkane, alkene, or alkyne.

Another object of the present invention is to provide a method for preparing a cyclodextrin inclusion complex containing an alkane, an alkene, or an alkyne, comprising introducing an alkane, alkene, or alkyne into an aqueous solution of a cyclodextrin, stirring said solution, collecting the crystalline inclusion complexes which precipitate out from said solution, and washing said crystalline inclusion complexes.

Yet another object of the present invention is to provide a method of delivering an alkane, an alkene, or an alkyne to a mammalian cell, either in vivo or in vitro, comprising contacting said cell with a complex of a cyclodextrin and an alkane, alkene, or alkyne, or with such compounds plus a biologically active molecule other than said alkane, alkene, or alkyne.

A further object of the present invention is to provide a method for testing the effects of an alkane, an alkene, or an alkyne on mammalian cells, comprising contacting said cells with a complex of a cyclodextrin and an alkane, alkene, or alkyne, or with a cyclodextrin and such compounds plus a biologically active molecule other than said alkane, alkene, or alkyne, and observing the effects of said complex on said cells.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

Figure 1:
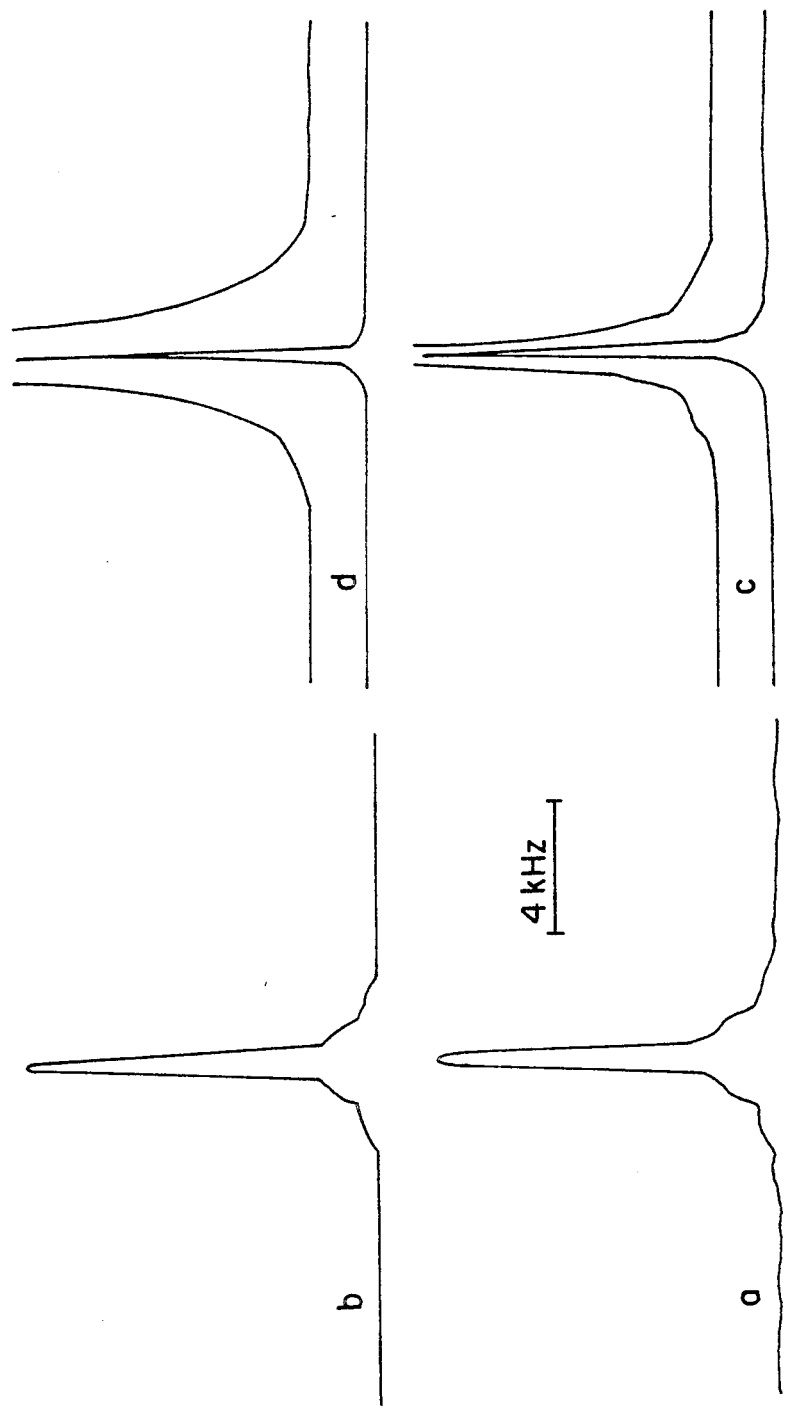
FIG. 1(a–d): $^2$H-NMR spectra of perdeuterated pristane in DPPC water (50 wt. % water) dispersions. The concentration of pristane is given in mol % of the sum of the molar concentrations of pristane and phospholipid: a, 1.0 mol %; b, 9.7 c, 16.3 mol %; d, 34.6 mol %.

The following detailed description of the invention is provided to aid those skilled in the art in practicing the present invention. Even so, the following detailed description should not be construed to unduly limit the present invention, as modifications and variations in the embodiments herein discussed can be made by those of ordinary skill in the art without departing from the spirit or scope of the present inventive discovery.

Physico-Chemical Studies

Abbreviations

β-CyD, β-cyclodextrin; D$_2$O, deuterium oxide; DMSO, dimethyl sulphoxide; DOPC, dioleoyl phosphatidylcholine; DOPE, dioleoyl phosphatidylethanolamine; DPPC, dipalmitoyl phosphatidylcholine; DSC, differential scanning calorimetry; NMR, nuclear magnetic resonance; PBS, phosphate buffered saline.

Chemicals

Synthetic L-α-dioleoyl phosphatidylcholine (DOPC), L-α-dioleoyl phosphatidylethanolamine (DOPE), and L-α-dipalmitoyl phosphatidylcholine-d$_{62}$ (DPPC) were purchased from Avanti Polar Lipids (Alabaster, AL, USA). The lipids were checked for impurities by thin layer chromatography and were judged to be at least 98 % pure. Pristane (2,6,10,14-tetramethylpentadecane, 96 % pure) was purchased from Aldrich Chemical Company (Milwaukee, WI, USA). Perdeuterated pristane was obtained from MSD Isotopes, Merck Division (Montreal, Canada). Deuterium oxide (minimal isotopic purity 99.9 atom% deuterium) was from MSD Isotopes (Merck, Rahway, NJ, USA), deuterium depleted water was from Cambridge Isotope Laboratories (Woburn, MA, USA), Tris (enzyme grade) was from BRL (Gaithersburg, MD, USA), sodium chloride was from Mallinckrodt (Paris, KY, USA), and β-cyclodextrin was from Sigma (St. Louis, MO, USA).

NMR

Sample preparation

A. Lipid mixtures of DOPE/DOPC (molar ratio 3:1) were prepared by dissolving both lipids in chloroform/methanol (2:1, v/v). The solvent was first removed in a stream of nitrogen and then in vacuum. About 50 mg of the dry lipids or lipid mixture were put into short Pyrex glass tubes with an outer diameter of 8 mm. Pristane was added to the dry lipid using a microsyringe.

The exact amount of lipid and pristane was determined with microbalances. Pristane concentrations given in mol % are calculated on the basis of the dry weight of the lipid in the respective sample. After the addition of pristane the tubes were closed with rubber stoppers. On the next day, water was added to prepare a 50 wt. % lipid-in-water dispersion.

B. Part of the samples (containing less than 10 mol % pristane) were prepared using stock solutions of pristane in chloroform. 50 mg of the matrix lipid were dissolved in an appropriate volume of the stock solution. The chloroform was removed first in a stream of nitrogen and then by vacuum (10 min). The samples were kept for a further 7 to 12 hours in a desiccator under reduced pressure. The rate of evaporation of pristane was checked with a pure sample of pristane in the same desiccator and a loss of only 1.5 % pristane was detected. For measurements on samples containing deuterated lipid or pristane, deuterium-depleted water was added. The glass tubes were sealed in a flame. Sample contents were mixed and pelleted by centrifugation. Prior to the NMR measurements, the samples were stored for several days at room temperature, except for DPPC-d$_{62}$ samples that were kept at 50° C.

Measurements

NMR measurements were performed on a Bruker MSL 300 spectrometer using a high power probe with an 8 mm solenoidal sample coil which was doubly tuned for $^{31}$P and $^1$H at 121.513 MHz and 300.133 MHz, respectively. Gated broadband decoupled $^{31}$P spectra were observed with a phase cycled Hahn echo sequence as described in (40). A delay time between the 90° and 180° pulse of 100 μs was chosen. Accumulation was started at the top of the echo. Typically 1024 scans with a recycle delay time of 1 s were accumulated. $^2$H NMR spectra were observed using the same 8 mm solenoidal sample coil as for $^{31}$P NMR but tuned for a resonance at 46.073 MHz. $^2$H NMR spectra were obtained using a quadruple echo sequence (41). The delay time between the two 90 pulses was 100 μs and the recycle delay time 1 s. Sample temperatures were adjusted using a Bruker temperature control unit.

Calorimetry

A Perkin-Elmer-DSC-2 was used to perform differential scanning calorimetry experiments. Dry DPPC was filled into aluminum pans. The weight of the dry lipid (=5 mg) was determined with Cahn electrobalances. Between 0.5 and 1 mg of pristane were added with a microsyringe to the dry lipid. Water was added in excess. Samples were sealed and equilibrated for 24 h at room temperature prior to the measurements. The calorimeter was calibrated against the known temperature (41.5° C.) of the gel-liquid crystalline phase transition of DPPC (42).

Solubilization of pristane

Pristane was solubilized by its molecular inclusion into β-cyclodextrin (β-CyD) in a novel coprecipitation procedure that was modified from a published method for complexing cinnarizine, a cerebral blood flow enhancer (43). Briefly, a bolus of pristane (final concentration 2 mM) was pipetted into a 4 mM β-CyD solution in distilled, deionized water and vigorously stirred on a simple benchtop mixer at ambient temperature for 4 days. The crystalline inclusion complexes which precipitated out of solution were washed two times in PBS (pH 7.4, 2,800×g, 20 min) in order to remove remaining free β-CyD. Aliquots were stored at −20° C. Working portions were kept at 4° C. Alternatively, pristane was dissolved in plain DMSO. This can be accomplished without phase separation problems at an initial dilution factor of 1:200 (v/v) or greater. That corresponds to a stock concentration of pristane of about 14.6 mM. Using tritiated pristane, this factor was determined in experiments aimed at estimating the solubility limit of pristane in plain DMSO and the requirements for its further dilution in a DMSO/phosphate buffer with progressively decreasing concentrations of DMSO (data not shown).

Preparation of unilamellar liposomes 250 mg of DOPC were dispersed in 25 ml of 10 mM Tris, 10 mM NaCl, 0.02 % (w/v) sodium azide in $D_2O$. The pD was adjusted to 7.4 using 1N HCl. After initial vortexing the dispersion was sonicated with a Fisher Sonic Dismembrator, Model 300 (Artek Systems Corp., Farmingdale, NY, USA) with a tip sonicator at 60% power output for about 45 minutes. During sonication the dispersion was cooled using a ice-cold water bath. Prior to the experiments the dispersion was stored in a refrigerator at a temperature of 4° C.

Uptake of pristane into liposomes

The incorporation of pristane into model lipid bilayers was studied using $^3H$-pristane, DOPC liposomes, and Tris/NaCl/$D_2O$ buffer. $^3H$-pristane (specific activity 30 mCi/ml) was prepared according to the catalytic hydrogen exchange method and was purified (final radiochemical purity >95%) by silica gel chromatography using n-hexane as solvent (American Radiolabeled Co., St. Louis, MO, USA). The experiments were carried out in 13×51 mm polyallomer centrifuge tubes in a final volume of 3 ml. Liposome buffer (Tris 10 mM, NaCl 10 mM, $D_2O$, pH 7.0/pD 7.4), liposomes and $^3H$-pristane were pipetted in the given order into centrifuge tubes that were carefully vortexed after addition of each reactant and then adapted (20 min) to a temperature of 37° C. In different experiments, $^3H$-pristane was added either solubilized in DMSO or as an inclusion complex with $\beta$-CyD. Samples were incubated between 1 and 12 hours at 37° C. with intermittent vortexing every 15–20 min. Then the tubes were centrifuged (2 h, 150,000×g, 25° C.) in a Beckman L8-T70 Ultracentrifuge using a SW-Ti55 rotor. After centrifugation a lower $D_2O$ phase and an upper liposome phase were clearly separated. The lower $D_2O$ phase was carefully aspirated in a plastic 3 ml syringe with a 20 gauge, 1.5 inch needle. The upper liposome phase was left in the tube. Triplicates of both phases were counted in a Packard Tri-Carb 1500 liquid scintillation analyzer. The activities in both phases were compared to the total activity, thus allowing estimation of the uptake of pristane into liposomes, the concentration of free pristane in the $D_2O$ phase, and the amount of pristane adsorbed to the wall of the centrifuge tube.

Results

NMR a) DOPC + pristane-$d_{40}$

The $^2H$-NMR spectrum of free pristane appears as a single resonance line with a linewidth of the order of 100 Hz that is indicative of isotropic motions. As a consequence of the incorporation of pristane into the lipid bilayers, the molecular motions of pristane acquire a certain degree of anisotropy. This results in a splitting of the $^2H$-NMR lines into doublets due to the angular dependent quadrupolar interaction between the deuterium nucleus and the internal electric field gradient of C-D (carbon-deuterium) bonds. The magnitude of splitting depends on the average orientation of the particular C-D bond to the magnetic field and fast motions of that bond axis. The spectra in FIG. 1 represent so-called powder patterns of doublet splittings of pristane incorporated into non-oriented bilayers. It can be seen that the quadrupolar splittings of the methyl and methylene groups of pristane are poorly resolved and overlapping. While the largest of the overlapping splittings is in the order of 4 kHz, other quadrupolar interactions in the same molecule are only in the order of a few hundred Hz or less, thus contributing to a broadened isotropic signal. It is known that the broadening of doublets is caused by reorientation processes with a correlation times of the order of $10^{-4}$ s. Slow reorientations of pristane molecules during lateral diffusion along membranes with radii of curvature of 1 μm and less is the most appropriate explanation of the broadening (44, 45). In agreement with this explanation is the fact that the shape of spectra depends to a certain extent on the sample preparation itself. We demonstrated previously that the preparation procedures decisively determine the fraction of liposomes with smaller radii of curvature that form in aqueous dispersions (46, 47).

The shape of $^2H$ NMR spectra is independent of the amount of pristane at concentrations of up to 5 mol % in DOPC bilayers. Above this concentration, the quadrupolar splittings of pristane decrease slightly, while the intensity of the broadened isotropic component increases (FIG. 1). Unfortunately, it is impossible to distinguish between the spectral contribution of pristane moving isotropically in a separate phase from the methyl group signals of incorporated pristane that also have very small quadrupolar splittings. For this reason we are not able to give the exact concentration of pristane at which a truly isotropic pristane signal can be seen for the first time. Nevertheless, all data indicate a change in the orientation and/or motion of pristane molecules at concentrations above 5 mol %.

Figure 3:
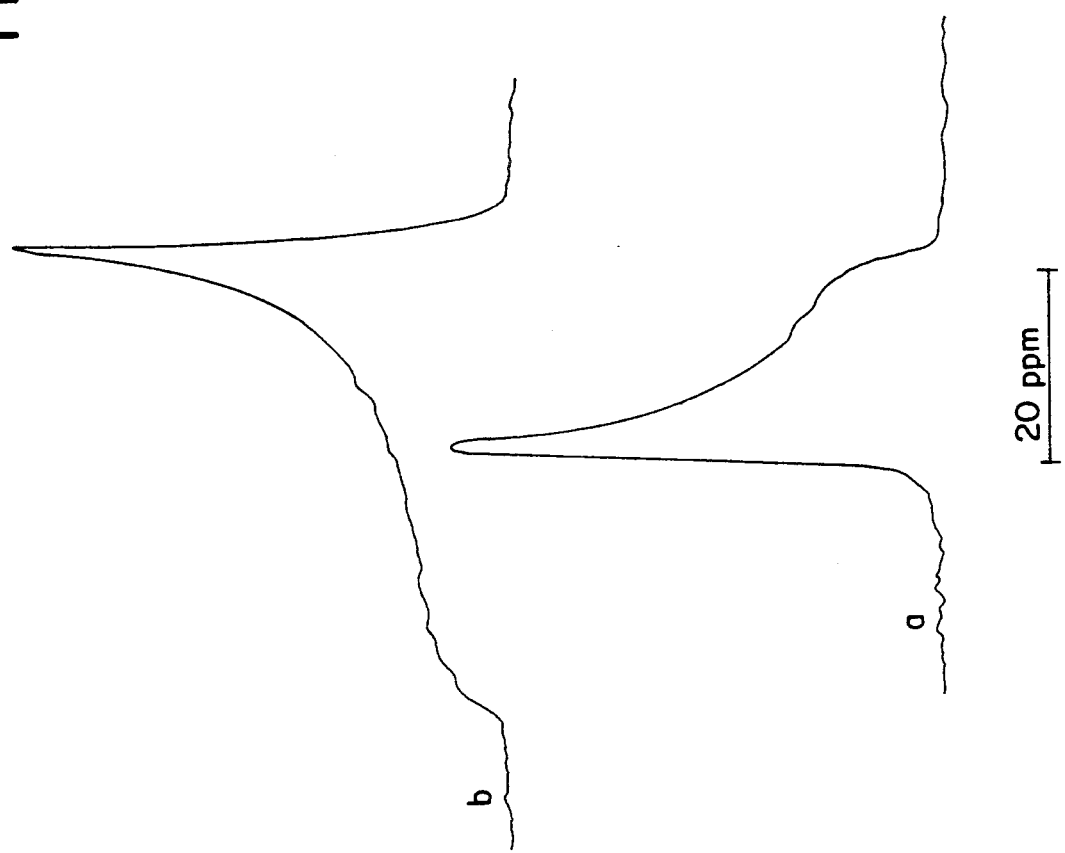
FIG. 3(a–b): $^{31}$P NMR spectra of DOPE (a, inverse hexagonal phase) and DPPC (b, lamellar phase) in the presence of pristane (a, pristane 4.2 mol %, b, pristane 3.7 mol %). The anisotropy of the chemical shift was +20.2 ppm (a) and −46.8 ppm (b respectively.

It is noteworthy that we reproducibly observed differences between spectra obtained after direct addition of pristane to the lipid matrix (see NMR sample preparation A., supra) and spectra recorded after prior simultaneous dissolution of pristane and lipids in chloroform (see NMR sample preparation B., supra). Direct addition results in a stronger isotropic component at concentrations as low as 3 mol %. On the other hand, the largest quadrupolar splittings, as reflected by the spectral width close to the baseline, at pristane concentrations as high as 16 mol % are still close to the values measured at 1 mol %. The $^{31}P$ NMR spectra of DOPC in the presence of increasing concentrations of pristane do not show any significant changes in the effective anisotropy of chemical shift of the lipid phosphate groups upon pristane addition (cf. FIG. 3). Indications of medium speed exchange processes that are connected to the decrease of the radii of curvature of liposomes after pristane addition can be found in both the $^2H$ NMR spectra of pristane-$d_{40}$ in DPPC water dispersions and the $^{31}P$ NMR spectra of lipids.

b) DPPC-$d_{62}$ + pristane

Figure 2:
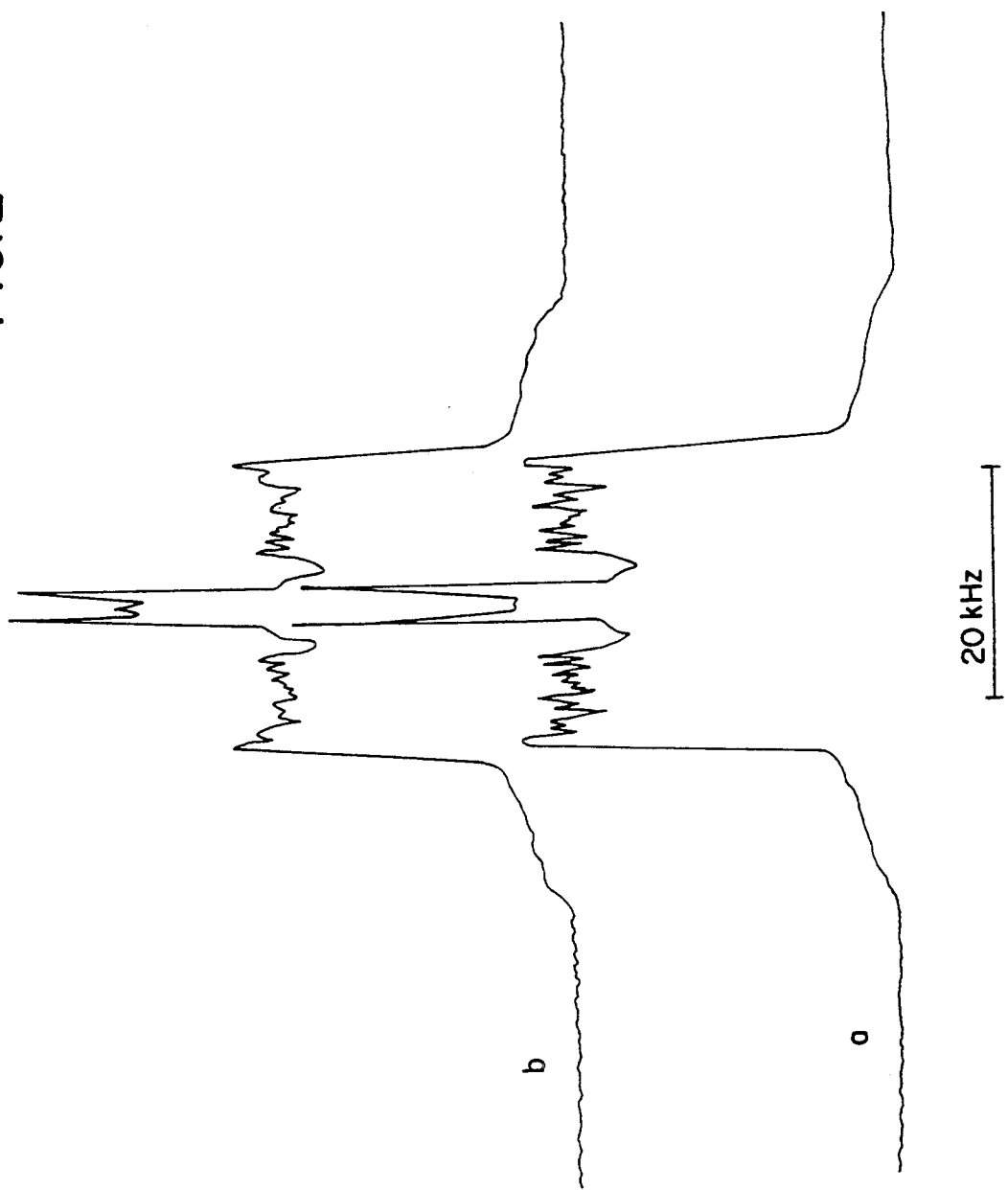
FIG. 2(a–d): $^2$H NMR spectra of (a) DPCC-$d_{62}$ (50 wt. %) in water without pristane and (b) with pristane (74.3 mol %) at 50° C.
Figure 4:
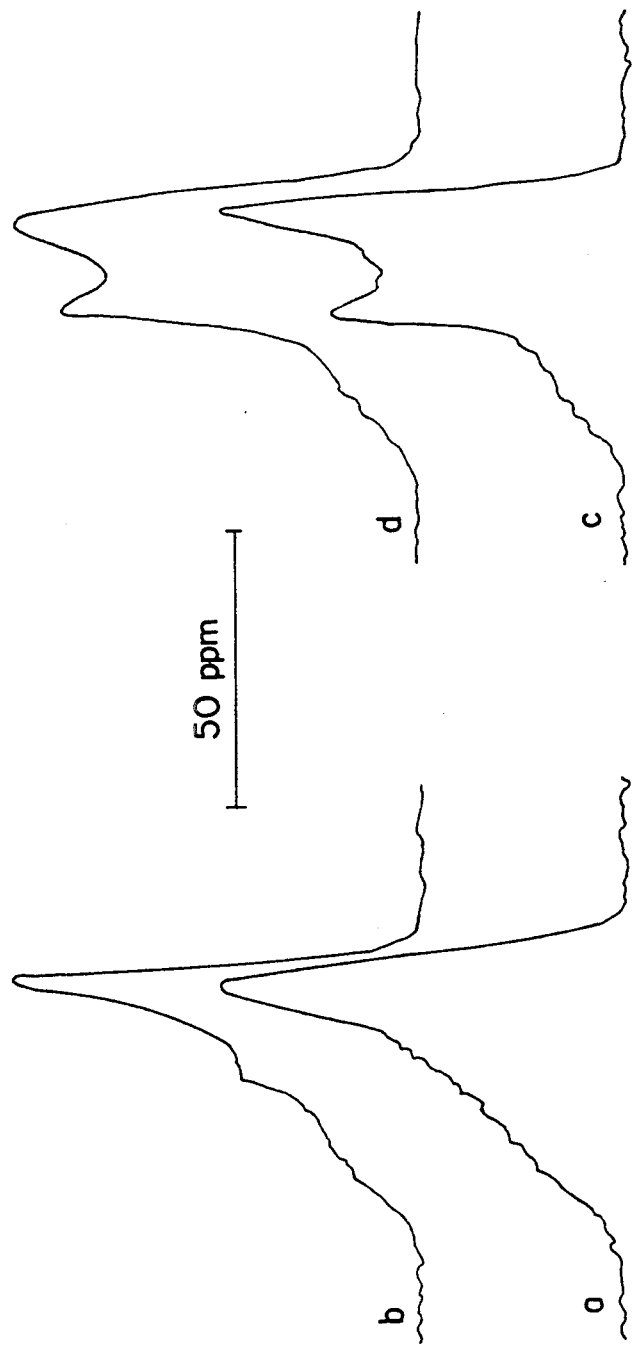
FIG. 4(a–d): Enhancement of the formation of an inverse hexagonal phase in DOPE/DOPC (3:1, mol/mol) mixtures by pristane. The concentration of pristane is given in mol % of the sum of molar concentrations of pristane and phospholipid: a, 5.5 mol %; b, 8.5 mol %; c, 12.7 mol %; d, 13.3 mol %.

The influence of the incorporation of pristane on the fatty acids of the phospholipids was investigated using fatty acid deuterated DPPC-$d_{62}$ in the presence of a large excess of pristane (74.3 mol %). The quadrupolar splittings observed for the DPPC-$d_{62}$, without added pristane were identical to values reported in (48). Pristane addition resulted in a slight broadening of resonance lines but had no influence on the position of resonance peaks. As in the case of $^{31}P$ NMR measurements, the broadening probably reflects the formation of particles with a radius of curvature of membranes less than 1 μm (FIG. 2).

c) DOPE/DOPC (3:1 molar)+pristane-d$_{40}$:

Rand et. al. (49) reported that addition of tetradecane to a DOPE/DOPC (3:1 molar) mixture transformed the lipid mixture from a lamellar to an inverse hexagonal phase. As shown in FIG. 4, pristane also caused the transformation of part of the lipid into a hexagonal phase in a dose-dependent fashion. Measurements of the anisotropy of chemical shift of the $^{31}$P NMR signal of DOPE in the hexagonal phase in the presence of pristane did not show any significant changes of lipid order parameters in comparison with samples not containing pristane. The $^2$H NMR spectrum of deuterated pristane in the hexagonal phase consists of poorly resolved overlapping quadrupolar splittings with a maximum splitting around 1 kHz (data not shown). Pristane-d$_{40}$ was incorporated into both lamellar and hexagonal phases in the same sample. Due to overlapping resonance signals it was not possible to determine the exact amount of pristane in both phases. Therefore, we are not able to predict whether pristane exhibits a preference for a particular phase, whether bilayer or non-bilayer.

Calorimetry

Figure 5:
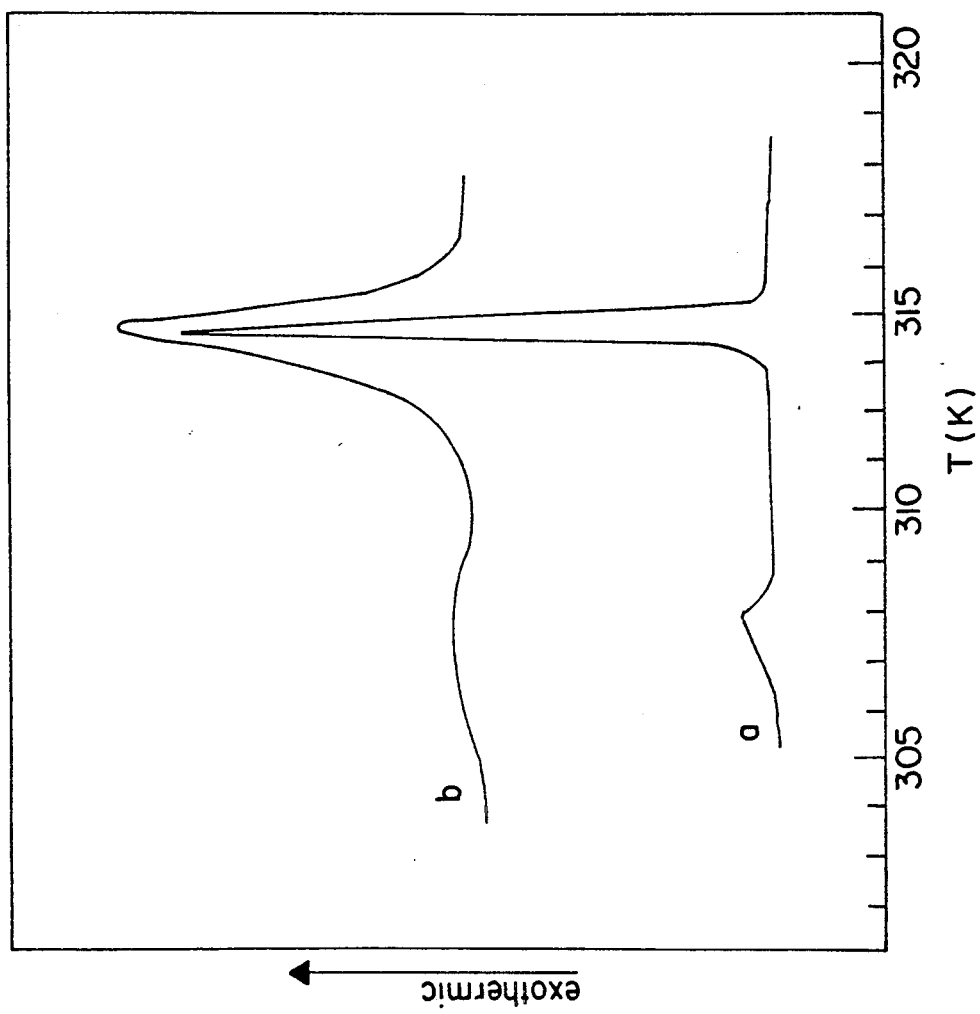
FIG. 5: DSC thermograms of dispersions of DPPC in water (a) without pristane and (b) with pristane (21.6 mol %).

Addition of an excess of pristane of up to 25 mol % to DPPC bilayers resulted in no measurable shift ($\pm 1°$ C.) of the phase transition temperature of DPPC from a gel to a liquid crystalline lamellar phase. However, the pretransition from the L$_\beta$ to the P$_\beta$ phase as well as the P$_\beta$/L$_\alpha$ phase transitions were significantly broadened (FIG. 5).

Uptake of pristane by liposomes

Figure 6:
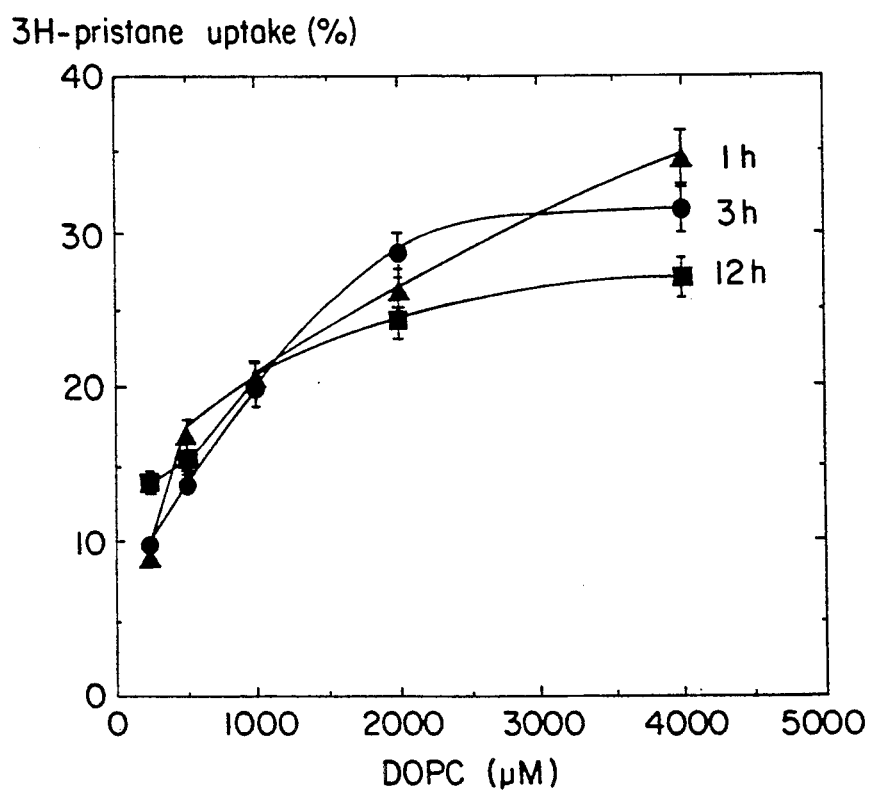
FIG. 6: Comparison of the uptake of pristane (final concentration 50 μM) solubilized in β-CyD into unilamellar DOPC liposomes during 1, 3, and 12 hours at T=37° C. Measurements were done in duplicates.

The uptake of pristane into model bilayer membranes was determined using tritiated pristane and small unilamellar DOPC liposomes with diameters of about 40 nm. The diameter of liposomes was determined by $^{31}$P NMR measurements after addition of the shift reagent PrCl$_3$. At ambient temperature, DOPC is in a liquid crystalline, lamellar phase that is equivalent to the phase state of membrane phospholipids in vivo. Deuterium oxide was used instead of water since previous methodologic experiments showed a better separation between the (upper) liposome phase and the (lower) aqueous phase after ultracentrifugation (data not shown). Pristane was added as an aqueous suspension of $\beta$-CyD/pristane inclusion complexes. First, the reproducibility of the uptake of pristane by three different DOPC liposome preparations was measured. The uptake proved to be reproducible with variations of about 10% in the maximal amount of pristane taken up (data not shown). In order to estimate the kinetics of the uptake of pristane, the incubation time at 37° C. was varied from 1 to 12 hours. FIG. 6 illustrates that the incorporation of pristane is complete after 1 hour and that prolongation of the incubation time up to 12 hours does not further increase the amount of pristane incorporated.

Figure 7:
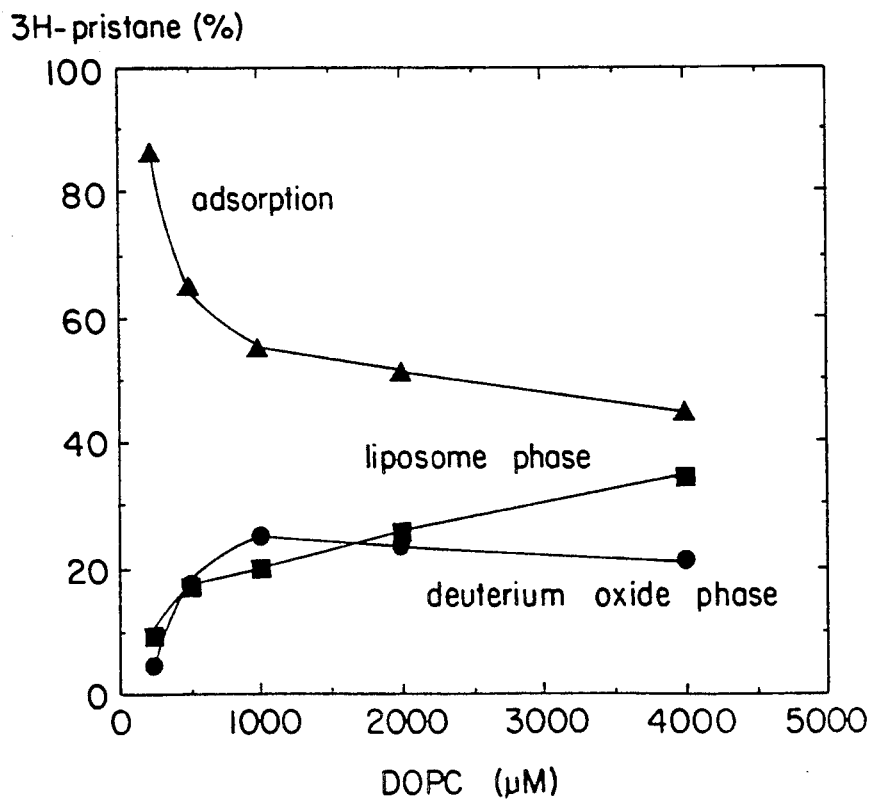
FIG. 7: Partitioning of β-CyD/pristane (final concentration 50 μM; t=12 h; T=37° C.) into the liposome phase (DOPC 250–4,000 μM), the D$_2$O phase, and the surface phase of the plastic vial.

The difference between using two different modes of solubilizing pristane on its subsequent incorporation into DOPC liposomes was analyzed. Pristane was added either solubilized in DMSO or as a molecular inclusion complex with $\beta$-CyD. The latter method disperses pristane at the molecular level by individually encapsulating each hydrophobic pristane molecule with a hydrophilic $\beta$-CyD coat. The amount of pristane in DOPC bilayers after incorporation via DMSO solubilization was smaller than 5% of the total pristane added (data not shown). Because of an experimental error of ±5% we were not able to determine the exact value. In contrast, solubilization of pristane in $\beta$-CyD led to substantially higher incorporation rates into liposomes. In FIG. 7, the partition of $\beta$-CyD/pristane into the three compartments of this simple system, i.e., the liposome phase, the D$_2$O phase, and the plastic surface of the centrifuge tube, is given. The partition proved to be quite different from that of DMSO/pristane where no significant adsorption to the plastic surface and a much lower uptake into the liposome phase were observed.

Significance of the Experimental Results

Incorporation of alkanes into lipid bilayers

Because of the wide use of alkanes in the formation of Black Lipid Membranes (BLM), numerous studies of n-alkane incorporation into lipid bilayers have been performed in the last 25 years. Pope et. al. (50) found that n-alkanes with chain lengths of 12 carbon atoms or less could be dissolved in amounts above 10 mol % in all bilayers examined. The same authors showed that the solubility of the longer chain alkanes at concentrations around 10 mol % alkane increased with increasing acyl chain length of the matrix lipid. Cholesterol in the membranes reduced the solubility for the longer chain alkanes, whereas the solubility increased with increasing temperature. Using methylated alkanes, White (51) showed that the molecular volume of alkanes has only a second order effect on alkane incorporation.

Alkanes in general do not change the area per molecule in the liquid crystalline phase. Short chain alkanes, however, increase the thickness of the hydrophobic portion of the bilayer. Neutron diffraction measurements (52) show that n-hexane forms a layer in the middle between the two bilayers. The mode of incorporation and the amount of incorporated material seems to derive from a complicated interplay between the enthalpy and entropy difference of alkanes in a bulk phase and in ordered membranes. The enthalpy of interaction increases if the alkanes line up with the lipid molecule, while a less ordered state of alkane molecules in the middle of the bilayers is preferred entropically. With increasing chain length the presence of alkanes in the center of bilayers is restricted to lower concentrations. The longer molecules are more likely to line up with the lipid fatty acid chains. Pope et. al. (50) relate the solubility of alkanes to an increased motional freedom of lipid carbohydrate chains in the middle of the bilayer. They conclude that alkanes dissolve in the disordered region in the middle of the membrane. The disordered region is larger for lipids with larger acyl chains and, therefore, these lipids incorporate more of the longer chain alkanes.

Incorporation of pristane into lipid bilayers

Addition of up to 5 mol % pristane to DOPC via a chloroform solution results in the formation of a homogeneous lipid pristane mixture in which all pristane molecules occupy identical binding sites. The apparent decrease of pristane order parameters at higher pristane concentrations is either connected with the occupation of binding sites of lower order in the same phase or the formation of other lipid structures containing increasing amounts of pristane. Possible candidates of other lipid structures containing pristane are pristane lenses covered by lipid monolayers and lipid micelles encapsulating pristane. How much of these structures is formed depends on the way pristane is added. Addition of pristane to the dry matrix lipid prior to sonication results in formation of the above mentioned structures at pristane concentrations as low as 3 mol %. The remaining portion of pristane is built into regular bilayers and maintains the quadrupolar splitting of pristane that is characteristic of low concentrations in bilayers. In other words, samples with plain pristane added directly to the dry lipid are nonhomogeneous and are characterized by high local concentrations of the compound. The less ordered or isotropic spectral components in these samples resemble the structures obtained in chloroform preparations at higher concentrations of pristane. The differences in free energy of pristane between these structures are small. As a result, different forms of the incorporation of pristane coexist with low exchange rates of pristane molecules between them.

The maximum quadrupolar splittings of pristane are only 25 to 30 % of the corresponding splittings of n-alkanes (53), indicating a higher motional freedom and/or different orientations of the individual methyl and methylene segments of pristane. This is supposedly caused by the influence of the bulky methyl groups of pristane. In contrast, the presence of pristane in a phospholipid bilayer does not seem to have any influence on the lipid order parameters in the headgroup and fatty acid regions. The mobility and conformation of phosphatidylcholine as measured by NMR are unchanged. In good agreement with that result is the fact that the quadrupolar splitting of pristane itself is not concentration dependent up to 5 mol %. At low concentrations, the binding sites for pristane between the lipid fatty acid chains are independent of each other.

Even high concentrations of added pristane (21.6 mol %, FIG. 5) in DPPC bilayers did not result in a measurable change in the gel-liquid crystalline phase transition temperature in the DSC measurements. Therefore, pristane molecules are unlikely to perturb intermolecular lipid interactions and membrane hydration to any significant extent. This is in contrast to n-alkanes, in which chain lengths of about 12 carbon atoms or less decrease the phase transition temperature of DPPC, while longer n-alkanes cause an increase (54). The chain length of pristane corresponds to that of n-pentadecane. If even-odd effects of the number of carbon atoms can be neglected, n-pentadecane can be expected to increase the phase transition temperature by about 6° C. But such an increase was not observed for pristane. We ascribe the deviation from the behavior of n-alkanes to the presence of bulky methyl groups along the chain in the pristane molecule. However, the DSC measurement did reveal broadened $L_{62}$, $P_{62}$, and $P_\beta/L_\alpha$ phase transitions which reflect an apparent loss of cooperativity after the incorporation of pristane into the DPPC bilayer. Such broadenings (and even a splitting) of the gel to liquid crystalline transition has also been described for n-alkanes (54). The reason for the observed loss of cooperativity might be a changed arrangement of the packing of the lipid bilayers. But we consider also the possibility that different structural isomers of pristane or impurities that are always present in commercial pristane preparations in low concentrations (55) may obscure true pristane effects. The above-mentioned inhomogeneities in arrangement of pristane in the lipid bilayer might also contribute to this effect.

Pristane, like other alkanes, increases the hydrophobic volume of bilayers. In lipid mixtures like DOPE/-DOPC which are capable of transforming into nonlamellar phases, pristane helps to reduce the packing stress in the hydrocarbon region, making the formation of a hexagonal lipid phase more likely. The formation of particles with radii of curvature less than $\mu m$ after pristane addition could be caused by a similar effect. That behavior might suggest that the rate of pristane incorporation depends strongly on membrane curvature (56), but until now we have no direct evidence for this. $^2H$ NMR of deuterated pristane in coexisting lamellar and hexagonal phases showed that pristane is located in both phases. Nonetheless, we can not rule out a slightly different uptake of pristane by one of the phases.

In the liposome experiments a maximal uptake of about 2 mol % pristane, relative to the dry weight of DOPC in the preparations, was observed. This amount is considerably lower than the 5 mol % of pristane homogeneously incorporated after its prior mixing with matrix lipid in chloroform. The lower uptake of pristane in the liposome experiments is not surprising considering that at least four different phases that compete for pristane need to be taken into account; i) the watery phase, ii) the $\beta$-CyD phase, iii) the plastic surface, and iv) the lipid phase. The amount of pristane in these phases depends on the concentration of binding sites and on the differences between them in free energy of pristane. Moreover, in the NMR experiments the lipid concentration was considerably higher (625 mM) than in the liposome experiments (4 mM). It is also important to realize that increased solubility of pristane in the watery phase caused by the addition of $\beta$-CyD improves the establishment of an equilibrium distribution of pristane between all binding sites, while at the same time decreasing the amount of pristane in different locations at thermodynamic equilibrium. The complexity of the thermodynamic picture is further illustrated by the effects of the vehicle on delivery of pristane to the liposome matrix. Solubilization of pristane in $\beta$-CyD, as compared to DMSO, led to significantly higher incorporation rates. This result is intriguing since these solubilization methods differ in principal. Whereas DMSO is an organic solvent that simply dissolves pristane, $\beta$-CyD disperses the compound at the molecular level by wrapping individual molecules with ring-shaped oligomers of glucose that have a hydrophobic molecular core and a hydrophilic surface. Thus, the $\beta$-CyD method solubilizes pristane in an aqueous phase in the complete absence of organic solvents Biological significance of the incorporation of pristance into biomembranes During the uptake of pristane by a cell, this hydrophobic compound should partition into the membrane interior, where it may act as a perturbant. Using a $>^{51}Cr$ release short-term cytotoxicity assay, we determined that the critical concentration of pristane (solubilized in $\beta$-CyD) capable of disrupting several cell lines during an 120 min incubation is about 200 $\mu M$, depending on the cell type used. Yet, the exact nature of this membrane perturbing/lytic activity has not been clarified. The only significant perturbation observed with NMR techniques was a tendency to form an inverse hexagonal phase after addition of pristane. At present it is unclear to which extent membrane stress caused by such a mechanism may be related to physiological membrane activity such as cell fusion, lysis, pore formation, vesiculation, and the activity of integral membrane proteins; any of these might contribute to the tumor inducing/promoting activity of pristane.

The generalization has been made that non-genotoxic carcinogens are primarily hydrophobic. It has further been proposed that in the absence of specific membrane receptor mediated effects, some compounds derive their activity solely from their hydrophobicity (57). This may be the case for pristane. Along these lines, $C_{10}$ to $C_{18}$ n-alkanes are tumor promoting in murine skin carcinogenesis (58). Moreover, a strong correlation between the length of the alkyl chains and their promotional activity in murine skin carcinogenesis has been observed for organic peroxides and hydroperoxides (59). The subsequent problem then becomes, how does the hydrophobicity alter cell functions? In this respect, it is recognized that the incorporation of external lipids into the cell membrane can cause diverse phenomena such as triggering of homeostatic processes aimed at preserving physico-chemical properties of the membrane (60), lipid exchanges near integral membrane proteins with potential alterations in conformation and activity (61), or modulation of enzyme activity through hydrophobic effects (62). Biochemical studies are warranted to see whether such processes might be brought about by pristane.

Finally, the finding of an enhancement of the uptake of pristane into unilamellar liposomes after its solubilization with β-CyD seems particularly important from a practical point of view, i.e., for devising experiments to test effects of pristane on cells in aqueous tissue culture media. In the past, such experiments have been frustrated by insufficient bioavailability of pristane after its dissolution in DMSO. This situation is very similar to other systems where the solubilization of alkanes proved to be the limiting step for studying their biological effect (63, 64). Using β-CyD-solubilization, it is now possible to obtain reproducible results when assaying toxicity, mitogenicity, and genotoxicity of pristane on various B lymphocyte cell lines, as described infra.

Biological Studies

Abbreviations

α-CyD, α-cyclodextrin; β-CyD, β-cyclodextrin; γ-CyD, γ-cyclodextrin; DMSO, dimethyl sulphoxide; EMEM, Eagle's minimal essential medium; HBSS, Hanks' balanced salt solution; LPS, lipopolysaccharide; PBS, Dulbecco's phosphate buffered saline (without $Ca^{2+}$ and $Mg^{2+}$); PC, L-α-phosphatidylcholine; DSPC, disteaoryl L-α-phosphatidylcholine; $^3$H-TdR, tritiated[-methyl-] thymidine.

Chemicals

α-Cyd, β-CyD, γ-CyD, L-α-phosphatidylcholine (PC, type II-S, approx. 17% phosphatidylcholine), disteaoryl L-α-phosphatidylcholine (DSPC, synthetic, purity ≈99%), and Triton X-100 were from Sigma (St. Louis, MO). Pristane (2,6,10,14-tetramethylpentadecane, 96% pure) and 3,5-diaminobenzoic acid (DABA, 99% pure) were purchased from Aldrich (Milwaukee, WI). $^3$H-pristane (specific activity 10.3 mCi/mmol) was prepared according to the catalytic hydrogen exchange method and was purified (final radiochemical purity >95%) by silica gel chromatography using n-hexane as solvent (American Radiolabeled Co., St. Louis, MO). $^3$H-TdR (20 Ci/mmol) and $^{51}$Cr (400–12,000 Ci/g) were obtained from NEN (Boston, MA). LPS (Escherichia coli 055:B5) was from Difco (Detroit, MI).

Cell lines and cell culture

The B-lineage lymphoma cell lines SJL-4 (subclone SJL-4/2) and NSF-1 (subclone NSF-1/12080-7) represent immunoblastic and follicular center cells, respectively (65). P388 is defined as an early B lymphoblastic lymphoma (66). All B cells were grown continuously in suspension culture in RPMI 1640 medium containing 10% (v/v) fetal calf serum (FCS), 200 mM L-glutamine, and 50 μM 2-mercaptoethanol at 37° C. in a humidified atmosphere containing 5% $CO_2$ in air. An initiated murine keratinocyte cell line, 308 (67), was cultured in EMEM medium supplemented with 8% (v/v) fetal calf serum and 1.2 mM $CaCl_2$. The 308 cells were plated in 60 mm dishes at a density of $2 \times 10^5$ cells/plate. The culture medium was changed 3 times/week.

Liposomes

Lipid vesicles were prepared from heterogeneous L-α-phosphatidylcholine (PC) and homogeneous disteaoryl L-α-phosphatidylcholine (DSPC) with a sonication technique modified from von Hofe et. al. (68). Briefly, the lipids were dissolved in chloroform/methanol (9:1, v/v) in a sterile glass centrifuge tube and the solvents were evaporated under a stream of nitrogen. Pristane and PBS, pH 7.4, were added to the bottoms of the tubes and the mixtures were sonicated with a sterilized sonicator probe at 60 W for 180 min on ice in order to form unilamellar vesicles. Sonicated preparations were centrifuged for 20 min at $20,000 \times g$. The optically clear center portion of the preparation, containing the unilamellar lipid vesicles, was separated from the coalescing micelles on the top of the tube and from the multilamellar lipid vesicles and debris on the bottom. Unilamellar lipid vesicles were divided into aliquots and stored at 4° C. For some experiments, aliquots were filtered through 0.80 μm, 0.47 μm, and 0.27 μm polycarbonate filters prior to use. The incorporation of pristane into PC liposomes proved to be much more effective than into DSPC liposomes (data not shown). Consequently, data on cytotoxicity experiments using liposome-solubilized pristane described here will only be given for PC liposomes.

Methods of preparing the β-CyD/pristane inclusion complex

The inclusion complex between β-CyD and pristane was prepared by modifying a published procedure for complexing cinnarizine, a cerebral blood flow enhancer, with β-CyD according to the coprecipitation and the neutralization methods (69). In the neutralization method, pristane (final concentration 2 mM) was added as a bolus to a β-CyD solution (4 mM in 0.1 N HCl). The mixture was adjusted to pH 11 with 1 N NaOH and subsequently neutralized to pH 7 with 1 N HCl. The crystalline precipitate which formed was washed twice in distilled, deionized water and resuspended in PBS, pH 7.4. In the coprecipitation method, a bolus of pristane (final concentration 2 mM) was pipetted into a 4 mM β-CyD solution in distilled, deionized water and stirred at room temperature for 4 days. The crystalline inclusion complexes which precipitated out of solution were washed two times in PBS and stored at 4° C. The coprecipitation method will be the only method further described.

$^{51}$Cr release cytotoxicity assay

Target cells ($2 \times 10^7$/ml) were labeled in HBSS with $^{51}$Cr (100 μCi/ml) for 1 hour at 37° C. and then washed three times in PBS, pH 7.4, with 7.5 mM glucose at 5°-10° C. Labeled cells ($1.2 \times 10^6$/ml) were incubated in a final volume of 0.5 ml with different concentrations of pristane for 2 hours in a 37° C. shaking water bath. The assay was stopped by addition of 3 ml ice cold HBSS. Cells were centrifuged at $400 \times g$ for 10 min at 5°-10° C. and 1 ml aliquots of the supernatant containing $^{51}$Cr released were transferred to plastic tubes and counted in a Gamma 4000 Beckman counter for 2 min. Positive controls representing 100% $^{51}$Cr release were determined by complete cell lysis with Triton X-100 (2%, v/v). Cytotoxicity is defined as ($Activity_{Sample} - Activity_{Background}$)/($Activity_{Positive\ contro}$ − $Activity_{Background}$). Background activity represents $^{51}$Cr release from negative (buffer only) control samples.

LPS-induced splenic B lymphocyte transformation

Normal proliferating splenic B lymphocytes were prepared from 8-12 week old BALB/cAnPt mice according to standard techniques. Briefly, splenic perfusates were freed of erythrocytes in hypotonic lysis buffer (0.004% NH$_4$Cl, 0.85% KHCO$_3$, 0.1% EDTA, pH 7.4) and seeded at a starting density of $1 \times 10^6$ cells/ml. The cells were cultured for 48-72 hours in serum-free medium (70) containing 0, 18.5, or 37.5 μg/ml *Escherichia coli* 055:B5 LPS. Cell counts and size distribution were determined with a model ZM Coulter counter. Blast cells were defined by the relatively stringent criterion as cells having a diameter larger than 14 μm.

$^3$H-TdR incorporation assay

Cells ($1 \times 10^5$/ml, 100 μl aliquots) suspended in double-supplemented medium (RPMI 1640 with 20% FCS, 400 mM L-glutamine, 100 μM 2-mercaptoethanol) were pipetted into 96-well culture plates containing 100 μl aliquots of serial dilutions (2-fold) of test sample (pristane or controls) diluted in RPMI/1% FCS. In each series, a well containing only cells and buffer was included to determine background counts. In order to minimize evaporation and temperature gradient effects the outer wells contained water only and were not used to assay samples. The plates were incubated at 37° C. in a humidified atmosphere of 5% CO$_2$. After 24-36 hours, 50 μl of pre-warmed $^3$H-TdR in culture medium were added to each well to give a final activity of 0.5-1.0 μCi/ml and the plates were further incubated for 4 hours. Cells were harvested in a Cambridge Scientific cell harvester and radioactivity was determined in a Packard LSC 1050 counter. The assay was carried out in a modified version for studying 308 cells. Briefly, the cells were plated in 60 mm dishes at a density of $2 \times 10^5$ cells/ml. After pulse-labeling the cells (1 μCi/ml, 60 min), cellular DNA from the entire plate was precipitated, hydrolyzed, and measured fluorometrically with 3,5-diaminobenzoic acid (71). $^3$H-TdR uptake was determined by liquid scintillation counting. The results are given as dpm/μg DNA.

Results

Characterization of the β-CyD/pristane inclusion complex a) Time course of inclusion complex formation

Figure 8:
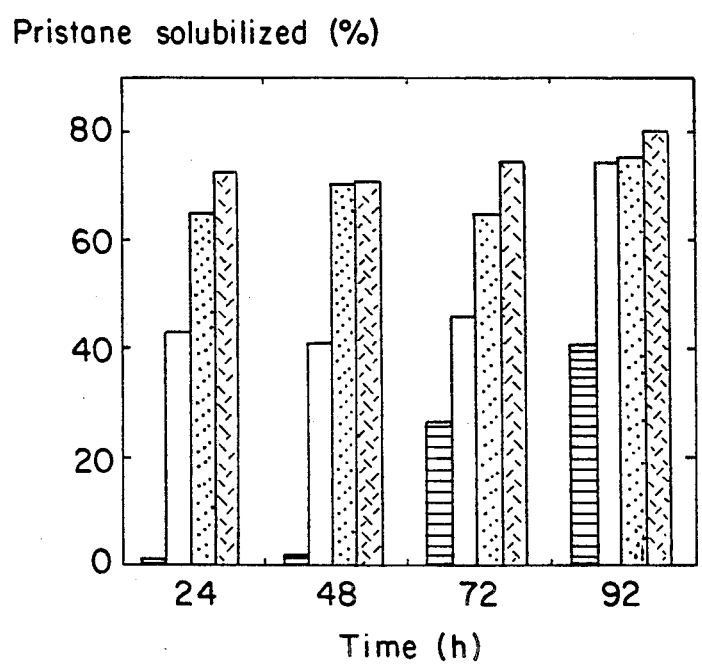
FIG. 8: Time course of inclusion complex formation. Pristane (final concentration 2 mM) was mixed with β-CyD (1, 2, 4 and 8 mM solutions) in water horizontal lines, open, dots, and cross-hatched bars, respectively) as described in Methods. In order to monitor the solubilization of pristane, the compound was mixed with $^3$H-pristane. The portion of pristane incorporated into β-CyD was determined by measuring radioactivity (liquid scintillation counting) in the inclusion complex precipitate at the given time points.

In order to estimate the rate of formation of the β-CyD/pristane inclusion complex, the time course of the molecular dispersion of pristane (2 mM final concentration) was measured using 4 different concentrations of β-CyD (1, 2, 4, and 8 mM) in water. This was accomplished by measuring the incorporation of $^3$H-pristane into the crystalline β-CyD/pristane inclusion complex. FIG. 8 shows that the time required to complex pristane was dependent upon the concentration of β-CyD used. A 2 or 4 mM β-CyD solution was sufficient to complex the pristane within 4 days and higher concentrations of β-CyD did not improve the solubilization process. The total recovery of complexed pristane after repeated washing and resuspension in an appropriate buffer was approximately 80%. Considering unavoidable losses of pristane during sample preparation (washing, centrifugation, etc.) and due to adsorption on the walls of the reaction vials, it may be assumed that the compound is solubilized quantitatively by the described method.

b) Stability and dissolution of β-CyD/pristane inclusion complexes

Figure 9:
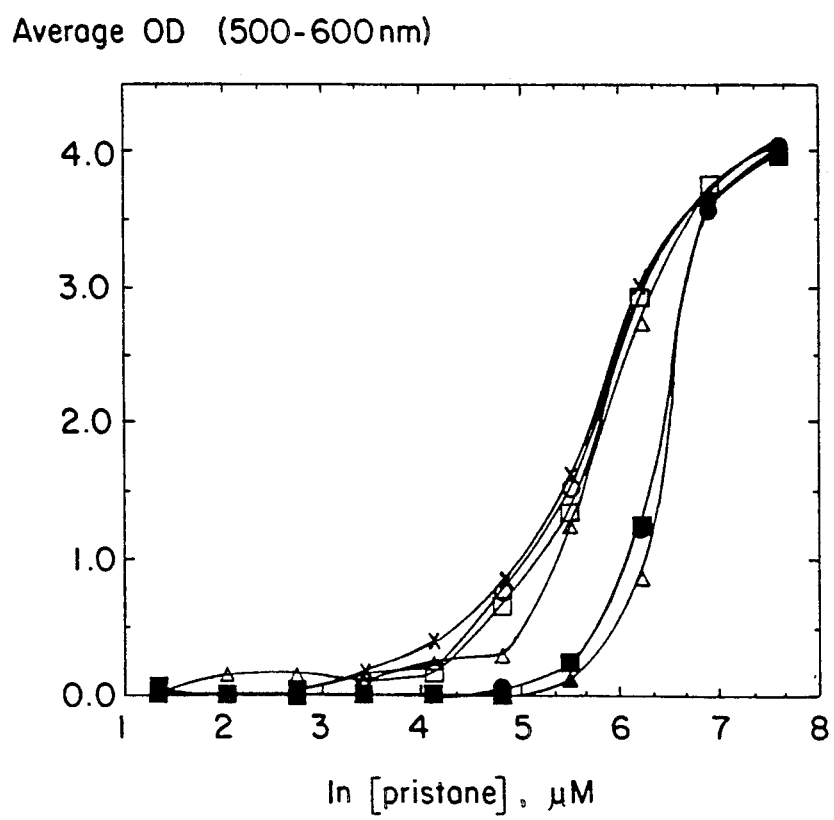
FIG. 9: Stability of the β-CyD/pristane inclusion complex. Suspensions of β-CyD/pristane inclusion complexes (10 μM –2 mM) were incubated either at ambient temperature (open symbols) or at 37° C. (closed symbols) for 40 min (circles), 70 min (squares) or 16 h (triangles). The starting suspension (zero time) is shown as x—x. Light scatter from the suspension of crystalline inclusion complex was measured in a diode array spectrophotometer as described in Methods.
Figure 10:
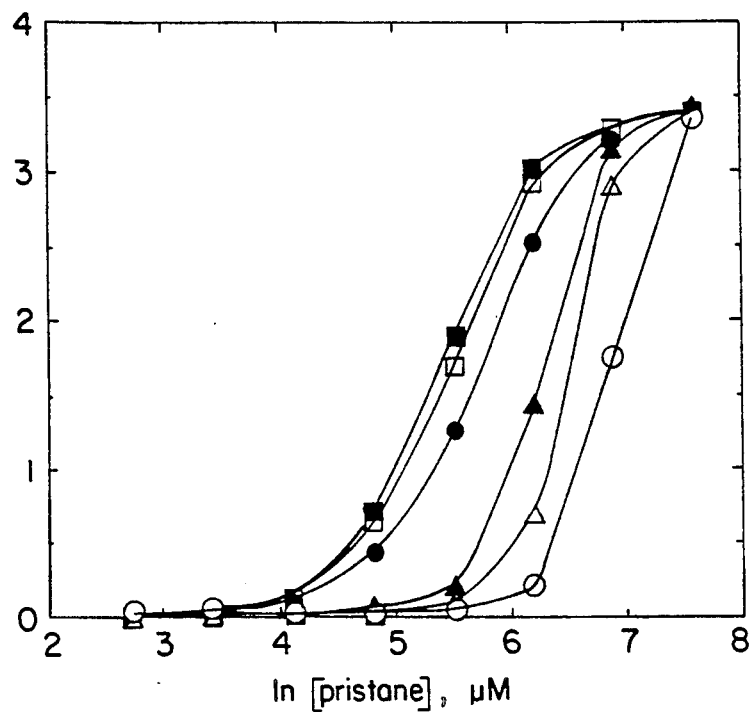
FIG. 10: Estimation of the dissolution of the β-CyD/pristane inclusion complex by organic solvents and/or detergents. β-cyclodextrin/pristane inclusion complex was suspended at the indicated concentrations in PBS containing either no additions (control, solid squares) or the following additions: 2% DMSO+2% ethanol (open squares); 5% DMSO+5% ethanol (solid circle); 1% Triton X-100 (solid triangle); 1% Triton X-100+2% DMSO+2% ethanol (open triangle); 1% Triton X-100+5% DMSO+5% ethanol (open circle). The location of the turbidity curve over this concentration range serves again as a measure of dissolution of crystalline inclusion complex (see also FIG. 2).

Preliminary data were collected to allow prediction of the general behavior of the complex in a biological assay system. Because it forms a turbid suspension in aqueous solutions, whereas β-CyD and pristane are both optically clear solutions, the concentration of inclusion complex can be followed by measuring light scattering in a spectrophotometer. To this end, the average optical densities of suspensions of β-CyD/pristane at 500-600 nm were measured on a Hewlett-Packard 8452A diode array spectrophotometer. FIG. 9 illustrates the high stability of the inclusion complex in water. The concentration of β-CyD/pristane required to give half-maximal turbidity is higher at 37° C. than at ambient temperature. Nonetheless, at either temperature, the complex is stable for at least 16 h. FIG. 10 shows preliminary findings on the dissolution of the β-CyD/pristane inclusion complex. It is evident that the addition of organic solvents such as ethanol or DMSO, as well as detergents such as Triton X-100, enhance the dissolution rate of the inclusion complex as reflected by the loss of turbidity. In addition, organic solvents increase the effect of Triton. As expected, the dissolution of inclusion complex in the presence of other solubilizers is enhanced by increased temperature (data not shown).

Biological testing of the β-CyD/pristane inclusion complex a) $^{51}$Cr release (cytotoxicity)

In order to evaluate the efficiency with which different solubilization principles allow pristane to interact with mammalian cells, a well-established short-term cytotoxicity assay was employed, i.e., the $^{51}$Cr release test. The rationale behind this approach was the assumption that the most likely primary target site of pristane at the cellular level is the cell membrane. It was anticipated that the potential for pristane to act as a nonspecific membrane perturbant subsequent to its partitioning into the lipid bilayer would be proportional the amount of pristane delivered to the target cell. Consequently, the percentage of $^{51}$Cr released per time unit should reflect the effectiveness of the solubilization vehicle employed. Moreover, equitoxic concentrations of pristane delivered by different carriers should allow a direct comparison of their respective efficiencies.

Figure 11:
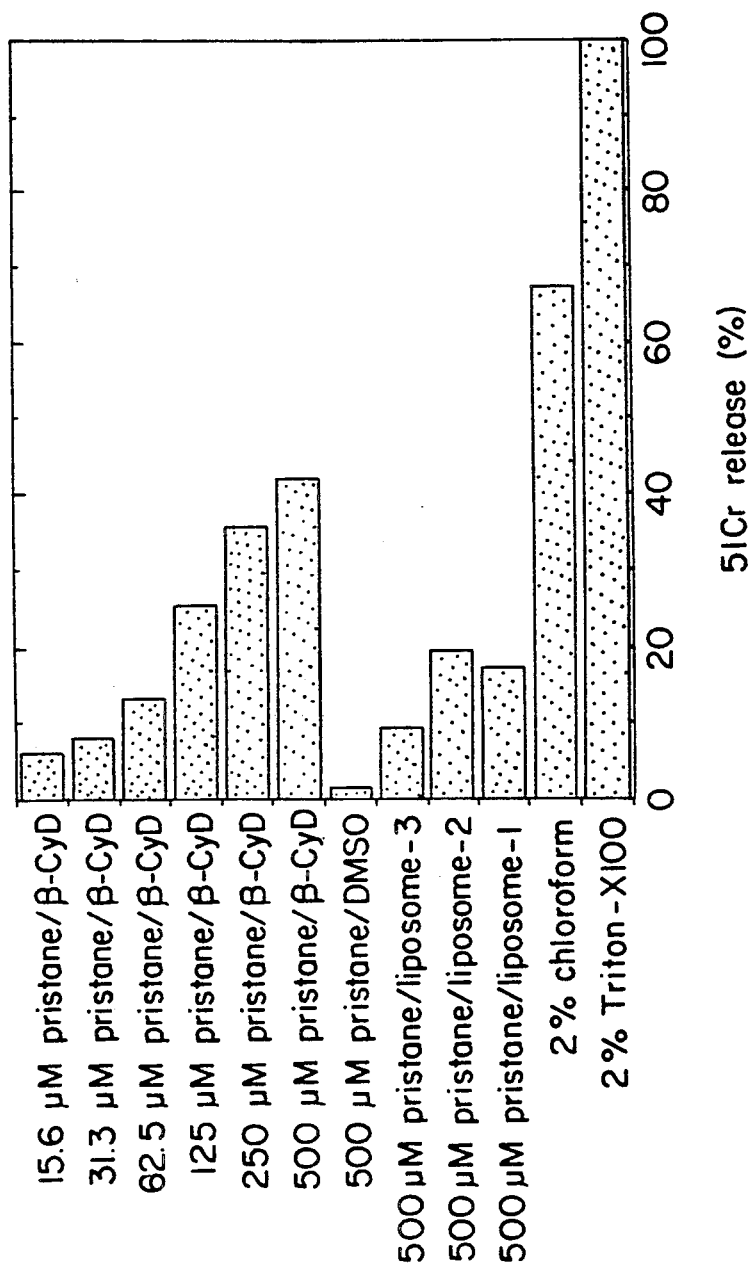
FIG. 11: Cytotoxicity of pristane to P388 cells as measured by the release of $^{51}$Cr. Pristane was solubilized either in DMSO, three different preparations of liposomes prepared from heterogeneous PC, or by molecular encapsulation in β-CyD. The solutions were added to P388 cells at 37° C. for 2 hours. Cytotoxicity was assayed as described in Methods. For comparison, cytotoxicity is shown for 2% chloroform (v/v) and for 2% Triton X-100 (v/v), which also serves as a standard for maximal $^{51}$Cr release.
Figure 12:
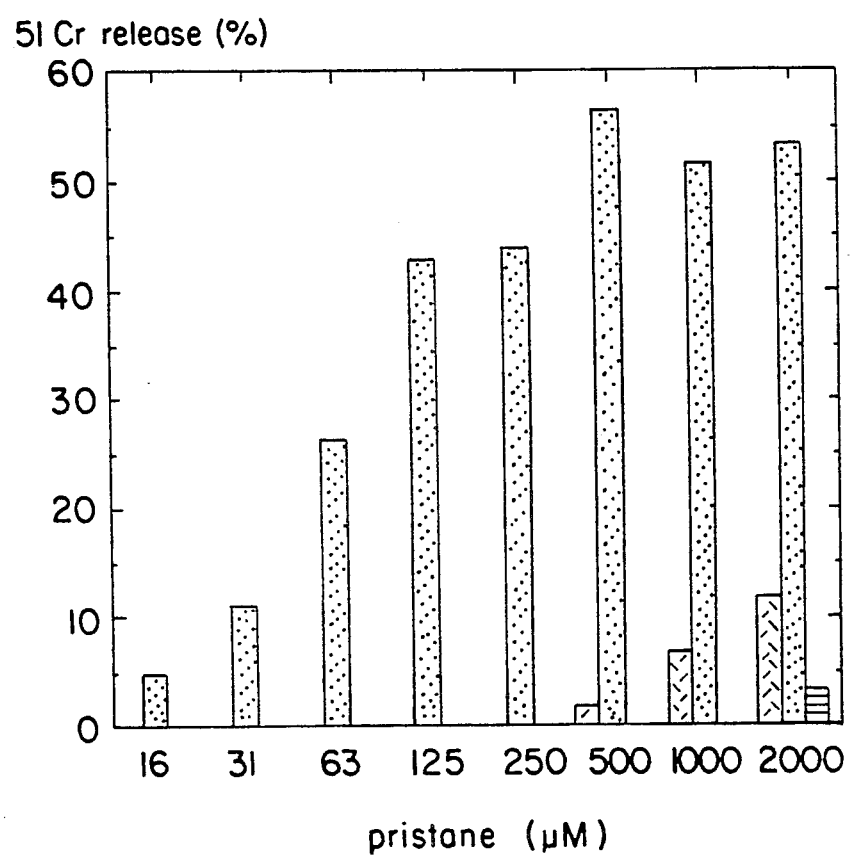
FIG. 12: Cytotoxic effects of pristane complexed by different CyD preparations. Inclusion complexes formed between pristane and aqueous solutions of α-, β-, and γ-cyclodextrin cross-hatched, dote, and horizontal lines, respectively) were prepared by the coprecipitation method as described in Methods. Cytotoxicity in NSF-1 cells was measured with the $^{51}$Cr release test after a 2 h incubation with the indicated concentrations of inclusion complexes as described in Methods.

In a standardized procedure, cytotoxicity in P388 cells was compared for pristane solubilized in DMSO, PC liposomes, and β-CyD (FIG. 11). It is shown that the different solubilization methods differed widely in their capacity to introduce pristane to the cells, and that β-CyD was the most efficient vehicle. The relative efficacies of α-, β-and γ-CyD to deliver pristane to NSF-1 cells were also compared. These compounds contain rings of 6, 7 and 8 glucose moieties, respectively, and hence differ in the size of the hydrophobic core. The results indicate that γ- and α-CyD were effective in delivering pristane to the cells (FIG. 12), but less so than γ-Cyd. When β-CyD was employed, pristane concentrations as low as 50–100 μM were clearly cytotoxic depending upon the cell line studied and the length of the incubation time (data on the kinetics of pristane-induced $^{51}$Cr release not shown).

b) Inhibition of LPS-induced solenic B lymphocyte transformation

Figure 13A:
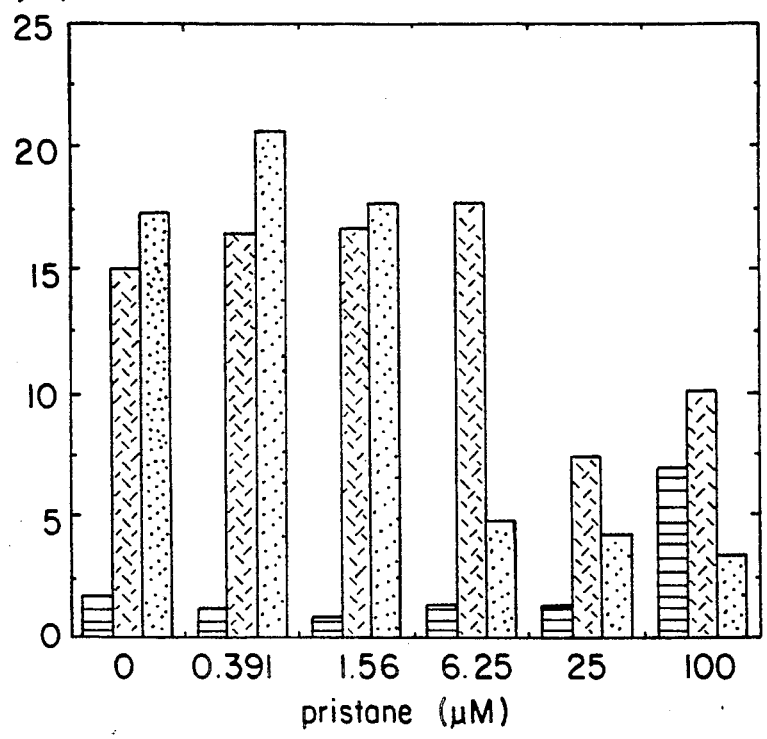
FIG. 13(A-B): Pristane (FIG. 13A) inhibits the LPS-induced transformation of splenic B lymphocytes to B lymphoblasts. LPS blasts were generated from BALB/c splenic cells that were cultured for 48 h in serum free medium containing no LPS (horizontal lines), 18.5 μg/ml LPS (cross-hatched), or 37.5 μg/ml LPS (dots). Blast formation and cell number were measured by Coulter Counter analysis as described in Methods. Addition of β-CyD alone had no effect on LPS-blast formation (FIG. 13B).
Figure 13B:
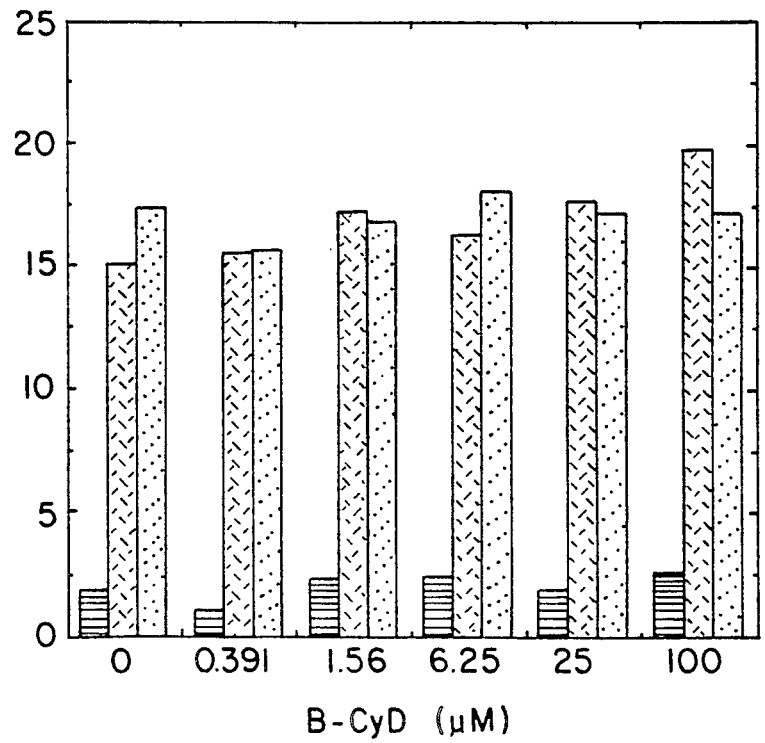

In a second set of experiments, the effect of pristane on a physiologic function of murine B lymphocytes was assessed. FIG. 13 shows that in comparison to cytotoxicity ($^{51}$Cr release), relatively low concentrations of pristane inhibited LPS-stimulated splenic B cell transformation. Although a thorough dose response relationship between pristane and LPS was not determined, it may be noted that approximately 25 μM pristane was required to inhibit the B cell transformation induced by a low dose of LPS (18.5 μg/ml), whereas 6.25 μM pristane was sufficient to inhibit the transformation induced by 37.5 μg/ml LPS, thus pointing to a differential effect of pristane dependent upon the degree of stimulation of the B cells (FIG. 13A). Addition of β-CyD alone had no effect on LPS-blast formation (FIG. 13B).

c) Growth-modulating effects of pristane complexed with β-CyD.

Figure 14:
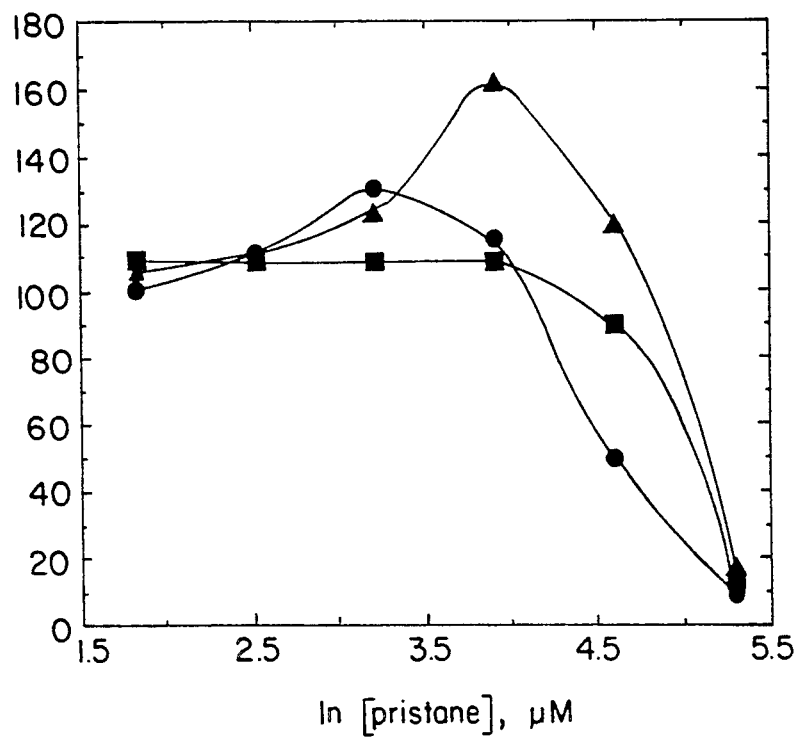
FIG. 14: Effect of pristane on $^3$H-TdR incorporation. Pristane was added at time zero at the indicated concentrations to SJL-4 cells (circles), P388 cells (squares), or an initiated keratinocyte cell line (308 cells, triangles. $^3$H-TdR incorporation assay was performed as described in Methods. Data are from three independent experiments run in triplicate. Standard deviations were less than 10% and are not shown. Pristane was added as an inclusion complex with β-CyD, and β-CyD served as the solvent control. Values are presented as % of control. β-CyD alone had no effect on $^3$H-TdR incorporation (data not shown).

In a third approach, potential growth-modulating effects of pristane on several B cell lines were examined by measuring $^3$HJ-TdR incorporation. FIG. 14 illustrates a modest increase in $^3$H-TdR uptake in SJL-4 cells (~30%) at concentrations around 25 μM. In contrast, this effect was not observed in P388 cells. A cell line completely unrelated to the lymphocytic lineage has also been employed, initiated mouse keratinocytes (308 cells), to test the effects of pristane on cell growth. Pristane was found to be maximally mitogenic at a subtoxic concentration of 50 μM as reflected by a significant (~60%) increase in $^3$H-TdR incorporation in comparison to the solvent control. These $^3$H-TdR labeling experiments were repeated several times over a wide range of concentrations of pristane, but only the narrow concentration range around 5–50 μM pristane proved reproducibly to be growth-promoting. Concentrations of pristane higher than 50 μM were cytotoxic depending upon the cell line investigated.

Significance of the Experimental Results

The purpose of this work was to develop a reliable and effective solubilization method for pristane so that its direct effects on cells could be investigated. The problem of delivering pristane to mammalian cells in vitro is not trivial. In its pure form, pristane is not bioavailable. It is almost totally immiscible in water and hence cannot come into contact with a cell surrounded by an aqueous environment. In other systems where biological effects of alkanes have been studied, proper solubilization has been the limiting precondition for obtaining meaningful data (68, 72, 73). It is interesting to note that certain alkane-utilizing microorganisms (bacteria and fungi) release biosurfactants in order to facilitate uptake of hydrocarbon substrates (74). In order to determine whether a particular solubilization protocol was effective in delivering pristane to cells, effects on cell function were assayed. This was accomplished using well-established tests for cytotoxicity ($^{51}$Cr-release), proliferation ($^3$H-TdR incorporation), and mitogen-driven B cell development (LPS-blast formation). With these assays, it was assumed that a cellular response could only be achieved if pristane was incorporated into the cell, thus reflecting successful delivery. It was found that encapsulation in β-CyD was the most effective method for rendering pristane bioavailable. Hence, pristane was found to be cytotoxic at concentrations greater than or equal to 50 μM, mitogenic at subtoxic concentrations (e.g., 25–50 μM), and inhibitory to LPS-blast formation at even lower concentrations (6.25–25 μM). The concentration of all of these effects was dependent upon the cell line and type being examined.

Limitations of using conventional solubilization methods to deliver pristane to mammalian cells Conventional methods of solubilizing alkanes in aqueous media rely either on organic solvents (with/without surfactants) or on lipid vesicles such as uni- or multilamellar liposomes. Employment of organic solvents imposes severe biological drawbacks because many of them are highly toxic to cells. They can produce artifacts even at very low concentrations (72). Moreover, initial solubilization in an organic solvent does not guarantee that the lipophilic compound will remain dissolved after further dilution into an aqueous medium; the initial macroemulsion that results from addition of a hydrophobic compound in a water-miscible organic solvent (e.g., DMSO) is not stable. This problem is circumvented somewhat by adding surface active compounds (biological detergents, tensids and co-tensids) to keep the hydrocarbon in solution. However, surfactants themselves alter and eventually disrupt cell membranes. They may also alter equilibria by forming micellar phases (75). The extent of adsorption of surfactants at the oil-water interface is largely determined by the nature of the hydrocarbon oil involved (87). Hence any solubilization system that involves the use of detergents has to be optimized for each individual alkane under consideration. This necessitates rather extensive solubilization studies prior to biological testing.

Lipid vesicles are also employed to deliver lipophilic compounds to mammalian cells. This method, too, contains potential artifacts since removal of lipophilic compounds from liposomes occurs only under participation of other membrane events such as fusion between the vesicles and the target cells (76) or lipid exchange (77, 78). Furthermore, retention of lipophilic materials within liposomes can be considerable (79). Hence, specific effects of the alkane of interest may be obscured by undesirable effects of the liposome itself. Some practical disadvantages are also inherent in using liposomes, such as poor reproducibility between different liposome preparations, as well as stability and storage problems (data not shown). The absence of a suitable protocol for delivering pristane to cells focused our attention on the need to develop an alternative method.

Advantages of using a β-CyD/pristane inclusion complex to deliver pristane to mammalian cells The advantages of solubilizing pristane (or a variety of other lipophilic guest compounds) by molecular complexation with β-CyD may be found by considering the unique properties of the host compound and the behavior of the complex in an aqueous environment. β-CyD is a relatively innocuous molecule which is neither metabolized nor absorbed by mammalian cells. Furthermore, it has practically no disadvantageous solvent effects (80). It is completely non-toxic to cells even at a concentration of 1 mM, which is the highest concentration tested (data not shown) Complexation with β-CyD improves the bioavailability of pristane by dispersing it at the molecular level, thereby increasing the solubility of the alkane in water and allowing facilitated partitioning into the cell membrane (81). The β-CyD/pristane complex forms a stable suspension in tissue culture media. When mixed with cells, pristane partitions from the less hydrophobic cyclodextrin cavity to more hydrophobic absorption sites in the lipid bilayer of the cell membrane.

Another positive feature of delivering pristane by means of an inclusion complex with β-CyD is highlighted by the concept of content-uniformity (82). It is extremely difficult to control or define the actual concentration of a compound that has both low solubility in water and a low effective concentration range. For example, pristane is practically insoluble in water and is effective in the present biological tests at micromolar concentrations. In most cases, conventional methods that employ watermiscible solvents to dissolve an alkane are insufficient to reliably and reproducibly disperse small amounts of the alkanes in aqueous media. This is because of the tendency of the alkanes to coalesce and form a separate phase with a trend toward an increase in particle size (83). In contrast, encapsulation of the compound in a suitable host molecule keeps the alkane dispersed at the molecular level. The finding that β-CyD proved to be the best cyclodextrin for this purpose was not unexpected because the ability to form an inclusion complex in solution is mainly determined by the cavity size of cyclodextrins. Thus, α-CyD is most useful for molecules smaller than benzene, β-CyD is used for compounds larger than benzene rings but smaller than benzo(a)pyrene, and γ-CyD is used for larger molecules (84).

The preparation of β-CyD/pristane inclusion complexes establishes a new system for testing the effects of pristane and other alkanes on mammalian cells in vitro. Further physicochemical studies are warranted in order to define the stability constant, equilibrium phase solubility diagram, crystal structure, etc. of the inclusion complex. It should be possible to optimize the delivery system by using substituted cyclodextrins which have a higher aqueous solubility than β-CyD. In addition, the preparation of an inclusion complex between β-CyD and pristane may allow for the conversion of pristane from an oily liquid into a microcrystalline solid which may be dried, stored and packaged as a powder or a tablet. Since cyclodextrins bear the potential to harbor two different compounds simultaneously, it is possible to deliver the test compound together with a potential modulator of its function (85). For example, the preparation of a ternary γ-CyD/pristane/indomethacin inclusion complex may make it possible to study the effect of pristane on cells in the presence of a drug known to inhibit murine plasmacytomagenesis (86).

Complexes of cyclodextrins With Other Alkanes, Alkenes, and Alkynes

The present method of complexing an alkane with cyclodextrins can be applied to any alkane, alkene, or alkyne, including aliphatic (open chain and cyclic) and aromatic compounds, for which there is a suitably sized cyclodextrin. This is defined by the stability constant of the complex, and is mainly determined by the hydrophobicity, relative size, and geometry of the alkane, alkene, or alkyne. In general, complex formation will not take place when the guest compound is either too large or too small to fit in the host cavity. Guest compounds do not, however, have to fit completely into the CyD cavity, but the efficiency of solubilization is improved for compounds that do. With respect to the upper size limit, longer or branched guests can be encapsulated by "capping" the ends of the compound with two β-CyD molecules that are oriented in head-to-head fashion. Cyclodextrin complexation is a versatile method that is applicable to many alkanes, alkenes, and alkynes, and can be achieved via the routine method described supra. In general, the upper size limit for branched chain and cyclic compounds, including arenes, will be higher (about $C_{36}$) than for straight chain compounds, for which the upper limit is about $C_{22}$. There is no lower size limit, and therefore compounds such as methane and methanol can be employed.

Representative aliphatic and aromatic compounds which can be employed in the present invention include, but are not limited to, the following:

| Alkanes | Alkenes | Alkynes |
|---|---|---|
| n-pentane | pentene | pentyne |
| n-hexane | n-hexene | n-hexyne |
| n-heptane | n-heptene | n-heptyne |
| n-octane | n-octene | n-octyne |
| n-nonane | n-nonene | n-nonyne |
| n-decane | n-decene | n-decyne |
| n-undecane | n-undecene | n-undecyne |
| n-dodecane | n-dodecene | n-dodecyne |
| n-tridecane | n-tridecene | n-tridecyne |
| n-tetradecane | n-tetradecene | n-tetradecyne |
| n-pentadecane | n-pentadecene | n-pentadecyne |
| n-hexadecane | n-hexadecene | n-hexadecyne |
| etc., through $C_{22}$ | etc., through $C_{22}$ | etc., through $C_{22}$ |

Cyclized alkanes, alkenes, and alkynes useful in the present invention include, but are not limited to, for example, cyclopentane, cyclohexane, cycloheptane, cyclooctane, etc.

Branched chain (i-) alkanes useful in the present invention include, for example, i-pentane, i-hexane, i-heptane, etc.

Also useful in the present invention are singly or multiply oxygenated, halogenated, nitrogenated, sulfated, etc. derivatives of n-, c-, or i-alkanes substituted on any carbon atom, such as alcohols, alkylhalides, haloalkenes, haloalkynes, ethers, epoxides, aldehydes, ketones, carboxylic acids, etc.

Further useful compounds include functional derivatives of the aforementioned, such as acid chlorides, acid anhydrides, amines, chloramines, amides, esters, phenols, etc.

Specific, non-limiting examples of such compounds include chloroform, ethyl chloride, ethylbromide, 1- or 2-chloropropane, 1- or 2- chlorobutane, 1-, 2-, or 3- chloropentane, chlorohexane, chloroheptane, etc.; methanol, ethanol, propanol, butanol, pentanol, etc.; methylamine, ethylamine, ethylamide, etc.; saturated and unsaturated fatty acids such as octanoic acid, nonoic acid, decanoic acid, undecanoic acid, dodecanoic acid, myristic acid, palmitic acid, stearic acid, oleic acid, linoleic acid, linolenic acid, and arachidonic acid; isoprenoid compounds and derivatives thereof such as pristane, pristanol, pristanic acid, phytane, phytol, phytanic acid, etc.; carotenoid derivatives of isoprenoids such as $\beta$-carotene and limonene; mineral oils; fish oils; phytol; squalene and derivatives thereof, such as cholesterol; triglycerides; and complex mixtures of hydrocarbons including, but not limited to, petroleum fractions such as natural gasoline ($C_5$–$C_{10}$ and cycloalkanes), kerosene ($C_{12}$–$C_{18}$ and aromatics), and gas oil ($C_{12}$ and higher), including alicyclic and aromatic hydrocarbons, aromatic-aliphatic hydrocarbons (arenes), etc.

The type of CyD used is dictated by the compound being studied and the intended application. The unsubstituted CyDs that are currently available are $\alpha$-, $\gamma$-, and $\gamma$-CyD. These show differences in cavity size, solubility in water, etc. By substituting some of the hydroxyl groups in the CyDs with different functional groups, properties such as solubility and encapsulating capacity can be altered significantly. As an example, the main disadvantage of $\beta$-CyD, its low aqueous solubility, can be markedly improved by substituting a hydroxyl group on the sugars with an alkyl moiety (e.g., 2-hydroxymethyl, 2-hydroxyethyl, 2-hydroxypropyl, 3-hydroxypropyl, 2-hydroxyisobutyl derivatives of $\beta$-CyD). The inclusion complexes of methylated $\beta$-CyDs are highly water soluble, and are more stable. Alkylation also makes $\beta$-CyD surface active. Further modifications of CyDs include tosylation, mesitylation, perbenzoylation, amination, esterification, and etherification. Many applications for these substituted CyDs have already been described, e.g., as catalysts, pharmaceuticals (serum cholesterol depressants), plasticizers, etc. Substituted CyDs hold much promise for further improvements of the solubilization of alkanes in watery phases. CyD polymers, another class of modified CyDs, exist as cross-linked and matrix-coupled CyDs. These polymers are mainly used in chemical and biotechnological separation techniques; however, their application for delivering alkanes, alkenes, and alkynes to target cells appears readily feasible. This could be accomplished, for example, by coating tissue culture plates with a stationary CyD polymer phase.

Stoichiometry

The molar ratio of $\beta$-CyD and pristane in the present invention has not yet been determined. On the basis of published results on the crystal structures of various $\beta$-CyD complexes, a molar ratio of $\beta$-CyD:pristane of about 2:1 is predicted. This prediction is mainly based on published results that $\beta$-CyD inclusion complexes form dimers in aqueous solution, followed by subsequent crystallization in, commonly, channel-type, head-to-head aggregates. The prediction of the molar ratio is indirectly confirmed by the experimental finding that the 2:1 ratio proved to be optimal for complexing pristane by the coprecipitation method. However, for definite characterization of the $\beta$-CyD/pristane complex, spectroscopic methods such as circular dichroism, UV absorption, and NMR, as well as X-ray and neutron diffraction analysis of crystallized complexes, will be required. In spite of an expected molar ratio of $\beta$-CyD to pristane different from 1:1, it is still correct to use the term "monomolecular inclusion complex" to describe such complexes.

In summary, $\beta$-CyD primarily forms channel-type complexes, with the cyclodextrins arranged head-to-head. A rare exception is the cage type complex that forms only with small guests (e.g., methanol.$6H_2O$, ethanol.$8H_2O$). Secondarily, these channel type complexes form cage type superstructures.

Ternary Complexes

Ternary or three-component systems consisting of CyD, an alkane, etc., and a second guest could provide interesting tools to elucidate mechanistic aspects of the plasmacytomagenic activity of such compounds. The second guest may modulate the biological activity of the alkane. For example, indomethacin, and possibly other non-steroidal anti-inflammatory drugs, inhibit pristane-induced plasmacytomagenesis. By treating cells with a ternary complex containing both pristane or any other alkane, etc. and indomethacin, it is possible to test whether the drug inhibits the effect of the hydrocarbon directly. Similarly, inclusion of a second guest compound that can interact either with the hydrocarbon or with the target cell provides a method to enhance, inhibit, or modulate the biological activity of either compound. With respect to the hypothesis concerning the generation of genotoxic oxidation products of pristane by reactive oxygen intermediates, ternary complexes that include radical producing (e.g., EDTA/Fe chelates) or radical scavenging (e.g., low molecular weight antioxidants) compounds could be useful. Other feasible ternary systems may include certain cofactors for catalysis of site-specific reactions, or pharmacologically active compounds such as prostaglandins, retinoids, and sex hormones.

In theory, there is no reason to limit the number of potential guest compounds to only two. Depending on the size, net hydrophobicity, and geometry of the guest molecules, quaternary and larger complexes are possible, and are encompassed within the scope of the present invention. Examples of such complexes include, for example, pristane/indomethacin/copper complexed in gamma-CyD; EDTA or an amino acid/iron or copper-/an alkane such as n-dodecane or a fatty acid, fatty alcohol, or other lipid complexed in gamma-CyD; etc.

Non-limiting examples of second guest compounds which can be used to form ternary complexes with the alkanes, alkenes, alkynes, aromatics, etc. described supra include indomethacin; other non-steroidal antiinflammatory drugs such as aspirin, naproxen, ibuprofen, phenylbutazone, etc.; free radical-producing compounds such as transition metals, (iron, copper, nickel, etc.); chelates of EDTA (ethylenediamine tetraacetic acid), EGTA, amino acids (e.g., histidine), and nucleotides (e.g., ATP); paraquat; bleomycin; adriamycin; free radical scavenging compounds such as BHT, ethanol, DMSO, mannitol, cysteine, and derivatives thereof (e.g., N-acetyl-cysteine); and nitroxides (e.g., DMPO, TEMPO, TEMPOL, PBN, etc.).

Delivery of Inclusion Complexes to Cells

The cyclodextrin inclusion complexes of the present invention can be delivered to cells in vivo or in vitro.

Methods of delivering in vivo include, for example, parenteral administration, either i.v., i.m., or i.p., oral administration, or topical administration.

Methods of delivery in vitro include, but are not limited to, addition as a solution or powder to cells, tissues, or organs in culture, and the use of pre-coated tissue culture or petri dishes, or flasks.

The types of cells to which such cyclodextrin inclusion products can be delivered according to the methods of the present invention include, but are not limited to, prokaryotic cells such as bacteria and viruses, and eukaryotic cells such as animal cells, including mammalian cells, cells of higher plants, algae, and fungi.

Diagnostic Uses

The primary diagnostic uses of CyD inclusion complexes with alkanes and other hydrophobic compounds lie in areas of biological testing, particularly for toxic, genotoxic, mitogenic, and other biological effects. Specific applications comprise screening procedures for tumor initiating and/or promoting compounds, testing of volatile alkanes, alkenes, alkynes, and other chemicals in vitro as a comparison to inhalation types of studies, genotoxicity testing in pro- and eukaryotic tester systems such as the Ames test, SOS chromotest, etc., and studies on the effects of membrane-active compounds on signal transduction pathways, gene expression, chromatin structure, etc.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Literature Cited

1. Bryson, P. D. (1986). Hydrocarbons. In Comprehensive review in toxicology. Edited by P. D. Bryson. pp. 287–302, Aspen Systems Corp., Rockville, MD.
2. Rocchiccioli, F., Lageron, A. & Duboucher, C. (1987) Abnormal n-nonacosane storage in humans: detection by gas chromatography/mass spectrometry of tissue extracts. Biomedical and Environmental Mass Spectrometry 14, 481–485.
3. MacFarland, H. N. (1988). Toxicology of petroleum hydrocarbons. Occupational Medicine: State of the Art Reviews 3, 445–454.
4. Salvayre, R., Negre, A., Rocchiccioli, F., Duboucher, C., Marlet, A., Vieu, C., Lageron, A., Polonovski, J. & Douste-Blazy, L. (1988). A new human pathology with visceral accumulation of long-chain n-alkanes; tissue distribution of the stored compounds and pathophysiological hypotheses. Biochimica et Biophysica Acta 958, 477–483.
5. Nilsen, O. G., Haugen, O. A., Zahlsen, K., Halgunset, J., Helseth, A., Aarset, H. & Eide, I. (1988). Toxicity of $n$-$C_9$ to $n$-$C_{13}$ alkanes in the rat on short term inhalation. Pharmacology and Toxicology 62, 259–266.
6. Lester, D. E. (1979). Title ???. Progress in Food and Nutrition Sciences 3, 1–66.
7. Garrett's paper (3–4)
8. Moloney, S. J. & Teal, J. J. (1988). Alkane-induced edema formation and cutaneous barrier dysfunction. Archives of Dermatology Research 280, 375–379.
9. Anderson, P. N. & Potter, M. (1969). Induction of plasma cell tumours in BALB/c mice with 2,6,10,14-tetramethylpentadecane (pristane). Nature 222, 994-???.
10. Potter, M. (1987). Plasmacytoma development in BALB/c mice. Advances in Viral Oncology 7, 99–122.
11. Potter, M. (1990) Neoplastic development in B-lymphocytes. Carcinogenesis 11, 1–13.
12. Grant, D. J. W. & Higuchi, T. (1990). Solubility in and partitioning into water. In Solubility behavior of organic compounds (Techniques of chemistry, vol. XXI). Edited by D. J. W. Grant. pp. 355–398, John Wiley & Sons.
13. Gregoriadis, G. (1990). Immunological adjuvants: a role for liposomes. Immunology Today 11, 89–97.
14. Weber, E. (1987). Clathrate chemistry today some problems and reflections. Topics in Current Chemistry 140, 2–20.
15. Szejtli, J. (1984). Industrial applications of cyclodextrins. In Inclusion compounds, vol. III. Edited by J. L. Atwood, J. E. D. Davies & D. D. MacNicol. pp. 331–390, Adademic Press.
16. Szejtli, J. (1989). Downstream processing using cyclodextrins. TIBECH 7 170–174.
17. Pitha, J. (1984). Biomedical applications of complexation agents/solubilizers. Journal of Inclusion Phenomena 2, 477–485.
18. Bender, H. (1986). Production, characterization, and application of cyclodextrins. Advances in Biotechnological Processes 6, 31–71.
19. Horton, A. W., Bolewicz, L. C., Barstad, A. W. & Butts, C. K. (1981). Comparison of the promoting activity of pristane and n-alkanes in skin carcinogenesis with their physical effects on micellar models of biological membranes. Biochimica et Biophysica Acta 648, 107–112.
20. Slaga, T. J., Solanki, V. & Logani, M. (1983). Studies on the mechanism of action of tumor promoting agents: Suggestive evidence for the involvement of free radicals in promotion. In Radioprotectors and anticarcinogenesis. Edited by O. F. Nygaard & M. G. Simic, MG. pp. 471–485, Academic Press, Orlando, FL.
21. Baxter, C. S. & Miller, M. L. (1987). Mechanisms of mouse skin tumour promotion by n-dodecane. Carcinogenesis 8, 1787–1790.
22. Ho, F. C. S. and Fu, K. H. (1987) Br. J. Exp. Path. 68, 413–420.
23. Luquet, P., Cravedi, J.-P., Tulliez, J. and Bories, G. (1984) Ecotoxicol. Environ. Safety 8, 219–226.
24. Wooley, P. H., Seibold, J. R., Whalen, J. D. and Chapdelaine, J. M. (1989) Arthritis Rheumatism 32, 1022–1030.
25. Yerganian, G., Paika, I., Gagnon, H. J. and Battaglino, A. (1979) Prog. exp. Tumor Res. 24, 424–434.
26. Horton, A. W., Bolewicz, L. C., Barstad, A. W. and Butts, C. K. (1981) Biochim. Biophys. Acta 648, 107–112.
27. Bost, K. L., Garrett, L. R. and Cuchens, M. A. (1986) Carcinogenesis 7, 1257–1265.
28. Nobis, P. and Löhler, J. (1983) Haematol. Blood Transfusion 28, 280–281.
29. Anderson, P. N. and Potter, M. (1969) Nature 222, 994–995.

30. Garrett, L. R., Bost, K. L., Buttke, T. M. and Cuchens, M. A. (1987) Agents Actions 20, 104-112.
31. Garrett, L. R., Pascual, D. W., Clem, L. W. and Cuchens, M. A. (1987) Chem.-Biol. Interactions 61, 249-263.
32. Bly, J. E., Garrett, L. R. and Cuchens, M. A. (1990) Cancer Biochem. Biophys. 11, 145-154.
33. JanZ, S., Brede, O. and Müller, J. Carcinogenesis, in press.
34. Shacter, E., Beecham, E. J., Covey, J. M., Kohn, K. W. and Potter, M. (1988) Carcinogenesis 9, 2297-2304.
35. Freund, Y. R. and Blair, P. B. (1982) J. Immunol. 129, 2826-2830.
36. Kripke, M. C. and Weiss, D. W. (1970) Int. J. Cancer 6, 422-430.
37. Platica, M., Bojko, C., Steiner, G. and Hollander, V. P. (1980) Cancer Res. 40, 2229-2233.
38. Nordan, R. P. and Potter, M. (1986) Science 233, 566-569.
39. Le Bon, A. M., Cravedi, J.-P. and Tulliez, J. E. (1988) Lipids 23, 424-429.
40. Rance, M. and Byrd, R. A. (1983) J. Mag. Res. 52, 221-240.
41. Davis, J. H., Jeffrey, K. R., Bloom, M., Valic, M. I. and Higgs, TP (1976) Chem. Phys. Lett. 42, 390-394.
42. Mabrey, S. and Sturtevant, J. M. (1976) Proc. Natl. Acad. Sciences (USA) 373, 3862-3866.
43. Tokumura, T., Ueda, H., Tsushima, Y., Kasai, M., Kayano, M., Amada, I., Machida, Y. and Nagai, T. (1984) J. Inclusion Phenomena 2, 511-521.
44. Burnell, E. E., Cullis, P. R. and DeKruijff, B. (1980) Biochim. Biophys. Acta 603, 63-69.
45. Gawrisch, K., Stibenz, D., Möps, A., Arnold, K., LinB, W. and Halbhuber, K.-J. (1986) Biochim. Biophys. Acta 856, 443-447.
46. Gawrisch, K., Richter, W., Möps, A., Balgavy, P., Arnold, K. and Klose, G. (1985) Studia Biophys. 108, 5-16.
47. Klose, G., König, B., Meyer, H. W., Schulze, G. and Degovics, G. (1988) Chem. Phys. Lipids 47, 225-234.
48. Davis, H. D. (1979) Biophys. J. 27, 339-358.
49. Rand, R. P., Fuller, N. L., Gruner, S. M. and Parsegian V. A. (1990) Biochemistry 29, 76-87.
50. Pope, J. M., Littlemore, L. A. and Westerman, P. W. (1989) Biochim. Biophys. Acta 980, 69-76.
51. White, S. H. (1977) Ann. N. Y. Acad. Sci. 303, 243-265.
52. White, S. H., King, G. I. and Cain, J. E. (1981) Nature 290, 161-163.
53. Ward, A. J. I., Friberg, S. E., Larsen, D. W. and Rananavare, S. B. (1984) J. Phys. Chem. 88, 826-827.
54. McIntosh, T. J., Simon, S. A. and MacDonald, R. C. (1980) Biochim. Biophys. Acta 597, 445-463.
55. Janz, S., Birkenfeld, T., Herzschuh, R. and Storch, H. (1989) Arch. Geschwulstforsch. 59, 415-422.
56. Gruen, D. W. R. and Haydon, D. A. (1980) Biophys. J. 30, 129-136.
57. McCoy, G. D., Rosenkranz, H. S. and Klopman, G. (1990) Carcinogenesis 11, 1111-1117.
58. Baxter, C. S. and Miller, M. L. (1987) Carcinogenesis 8, 1787-1790.
59. Slaga, T. J., Solanki, V. and Logani, M. (1983) in Radioprotectors and Anticarcinogens (Nygaard, O. F. and Simic, M. G., eds.) pp. 471-485, Academic Press, Orlando.
60. Cossins, A. R. and Sinensky, M. (1984) in Physiology of Membrane Fluidity, vol. 2 (Shinitzky, M., ed.), pp. 1-20, CRC press, Boca Raton.
61. Henry, G. D. and Sykes, B. D. (1990) Biochem. Cell Biol. 68, 318-329.
62. Jensen, J. W. and Schutzbach, J. S. (1989) Biochemistry 28, 851-855.
63. Delraso, N. J., Mattie, D. R. and Godin, C. S. (1989) In vitro Cell. Devel. Biol. 2, 1031-1038.
64. Miller, R. M. and Bartha, R. (1989) Appl. Environ. Microbiol. 55, 269-274.
65. Mushinski, J. F. (1987). Activation of cellular oncogenes in human and mouse leukemia-lymphoma: Spontaneous and induced oncogene expression in murine B lymphocytic neoplasms. Cancer Investigations 5, 345-368.
66. Bauer, S. R., Holmes, K. L., Morse, H. C. III & Potter, M. (1986). Clonal relationship of the lymphoblastic cell line P388D1 as evidenced by immunoglobulin gene rearrangements and expression of cell surface antigens. Journal of Immunology 136, 4695-4699.
67. Yuspa, S. H. & Morgan, D. L. (1981). Mouse skin cells resistant to terminal differentiation associated with initiation of carcinogenesis. Nature 293, 72-74.
68. von Hofe, E. H., Billings, P. C., Heidelberger, C. & Landolph, J. R. (1986). In vitro genotoxicity studies using complex hydrophobic mixtures: efficient delivery of a petroleum sample to cultured C3H/10T$\frac{1}{2}$ cells via lipid vesicle incorporation. Environmental Mutagenesis 8, 589-609.
69. Tokumura, T., Ueda, H., Tsushima, Y., Kasai, M., Kayano, M., Amada, I., Machida, Y. & Nagai, T. (1984). Inclusion complex of cinnarizine with $\beta$-cyclodextrin in aqueous solution and in solid state. Journal of Inclusion Phenomena 2, 511-521.
70. Shacter, E. (1987) Serum-free medium for growth-factor dependent and independent plasmacytomas and hybridomas. Journal of Immunological Methods 99, 259-270.
71. Kapp, L. N., Brown, S. L. & Klevecz, R. R. (1974). Detecting small quantities of DNA on CsCl gradients. Biochimica et Biophysica Acta 361, 140-143.
72. Ma, C. Y., Ho, C. -H., Quincy, R. B., Guerin, M. R., Rao, T. K., Allen, B. E. & Epler, J. L. (1983) Preparation of oils for bacterial mutagenicity testing. Mutation Research 118, 15-24.
73. Miller, R. M. & Bartha, R. (1989) Evidence from liposome encapsulation for transport-limited microbial metabolism of solid alkanes. Applied and Environmental Microbiology 55, 269-274.
74. Zajic, J. E. & Mahomedy, A. Y. (1984). Biosurfactants: Intermediates in the biosynthesis of amphipathic molecules in microbes. In Petroleum microbiology. Edited by R. M. Atlas. pp. 221-297, Macmillan Publishing Company, New York.
75. Pitha, J., Irie, T., Sklar, P. B. & Nye, J. S. (1988). Drug solubilizers to aid pharmacologists: amorphous cyclodextrin derivatives. Life Sciences 43, 493-502.
76. Seibicke, S., Zimmermann, H. P. & Haeffner, E. W. (1988). Fusion of lipid vesicles with ascites tumor cells and their lipid-depleted variants. Studies with radioactive- and fluorescent-labeled vesicles. Biochimica et Biophysica Acta 944, 487-496.
77. Nichols, J. W. (1988) Kinetics of fluorescent-labeled phosphatidylcholine transfer between nonspecific lipid transfer protein and phospholipid vesicles. Biochemistry 27, 1889-1896.

78. Herrmann, A., Zachowski, A. & Devaux, P. F. (1990). Protein-mediated phospholipid translocation in the endoplasmic reticulum with a low lipid specificity. Biochemistry 29, 2023-2027.
79. Kimelberg, H. K. & Mayhew, E. G. (1978). Properties and biological effects of liposomes and their uses in pharmacology and toxicology. Critical Reviews in Toxicology 6, 25-79.
80. Bar, R. (1989). Cyclodextrin-aided bioconversions and fermentations. TIBTECH 7, 2-4.
81. Uekama, K. & Otagiri, M. (1986). Cyclodextrins in drug carrier systems. CRC Critical Reviews in Therapeutic Drug Carrier Systems 3, 1-40.
82. Inaba, K., Wakuda, T. & Uekama, K. (1984). Prostaglandins and their cyclodextrin complexes. Journal of Inclusion Phenomena 2, 467-474.
83. Raabe, F., Janz, S. & Wolff, G. (1990). The effect of non-ionic surfactants on the SOS-inducing potency of 4-nitroquinoline-1-oxide in Escherichia coli PQ37. Journal of Basic Microbiology 30, 435-442.
84. Issaq, H. J. (1988). The multimodal cyclodextrin bonded stationary phases for high performance liquid chromataography. Journal of Lipid Chromataography 11, 2131-2146.
85. Kano, K., Hashimoto, S., Imai, A. & Ogawa, T. (1984). Three-component complexes of cyclodextrins. Exciplex formation in cyclodextrin cavity. Journal of Inclusion Phenomena 2, 737-746.
86. Potter, M., Wax, J. S. & Nordan, R. P. (1985) Inhibition of plasmacytoma development in BALB/c mice by indomethacin. Journal of Experimental Medicine 161, 996-1012.
87. Iranloye, T. A. (1985). Some factors affecting the self emulsification of hydrocarbon oils. Progress in Colloid Polymer Sciences 70, 119-126.

What is claimed is:

1. A complex of a cyclodextrin and a compound selected from the group consisting of an an alkene, and an alkyne.
2. The complex of claim 1, wherein said cyclodextrin is selected from the group consisting of α-cyclodextrin, β-cyclodextrin, γ-cyclodextrin, and a substituted derivative thereof.
3. The complex of claim wherein said alkene, or alkyne is linear or branched.
4. The complex of claim 1, wherein said alkene, or alkyne has at least twelve carbon atoms.
5. A complex of a cyclodextrin and an alkane wherein said alkane has at least twelve carbon atoms.
6. The complex of claim 5, wherein said alkane is an n-alkane or an i-alkane.
7. The complex of claim 6, wherein said alkane is selected from the group consisting of n-$C_{12}$ to n-$C_{19}$, and i-$C_{12}$ to i-$C_{19}$.
8. The complex of claim 7, wherein said alkane is selected from the group consisting of n-dodecane n-tetradecane, and n-hexadecane.
9. The complex of claim 7, wherein said i-$C_{19}$ alkane is pristane, 2,6,10,14-tetramethylpentadecane.
10. The complex of claim 5, which is a complex of β-cyclodextrin and pristane, 2,6,10,14-tetramethylpentadecane.
11. A complex of cyclodextrin and a compound selected from the group consisting of an alkane having at least twelve carbon atoms, an alkene and an alkyne which further comprises one or more biologically active molecules other than said alkane having at least twelve carbon atoms, alkene or alkyne.
12. The complex of claim 11, wherein said biologically active molecule is indomethacin.
13. The complex of claim 12, wherein said cyclodextrin is γ-cyclodextrin.
14. The complex of claim 12, wherein said alkane is an n-alkane or an i-alkane.
15. The complex of claim 14, wherein said alkane is n-dodecane, n-tetradecane, n-hexadecane, or prostane.
16. The complex of claim 11, wherein said complex comprises γ-cyclodextrin, pristane, and indomethacin.
17. A method for preparing a cyclodextrin inclusion complex containing an alkane having at least twelve carbon atoms, an alkene, or an alkyne, comprising the steps of:
introducing an alkane having at least twelve carbon atoms, an alkene, or an alkyne into an aqueous solution of a cyclodextrin;
stirring said solution; and
collecting the crystalline inclusion complexes which precipitate from said solution.
18. A method for delivering an alkane having at least twelve carbon atoms, alkene, or alkyne to a cell, tissue, or organ, comprising contacting said cell, tissue, or organ with a complex of cyclodextrin and a compound selected from the group consisting of an alkane having at least twelve carbon atoms, an alkene or an alkyne.
19. The method of claim 18, wherein said cell is a eukaryotic cell.
20. The method of claim 19, wherein said eukaryotic cell is selected from the group consisting of a higher plant cell, an animal cell, an alga, or a fungal cell.
21. The method of claim 20, wherein said animal cell is a mammalian cell.
22. The method of claim 18, wherein said cell is a prokaryotic cell.
23. The method of claim 22, wherein said prokaryotic cell is a bacterium or a virus.
24. The method of claim 18, wherein said contacting is carried out in vivo or in vitro.
25. The method of claim 24, wherein said contacting is carried out in vitro by coating a tissue culture plate with a complex of a cyclodextrin and an alkane, an alkene, or an alkyne.
26. A method for determining the effective selected from the group consisting of a toxic effect, a mitogenic effect, and a genotoxic effect of an alkane having at least twelve carbon atoms, alkene or alkyne or mammalian cells, comprising:
contacting said mammalian cells with a complex of cyclodextrin and a compound selected from the group consisting of an alkane having at least twelve carbon atoms, an alkene and an alkyne; and
determining said effect of said complex on said cells.
27. The method of claim 26, wherein said complex further contains a biologically active molecule other than said alkane, alkene, or alkyne.

* * * * *